US010758519B2

(12) United States Patent
Kiuchi et al.

(10) Patent No.: US 10,758,519 B2
(45) Date of Patent: Sep. 1, 2020

(54) UCP-1 EXPRESSION PROMOTER

(71) Applicant: Kao Corporation, Chuo-ku, Tokyo (JP)

(72) Inventors: Satomi Kiuchi, Chino (JP); Takatoshi Murase, Tochigi (JP)

(73) Assignee: Kao Corporation, Tokyo (JP)

( * ) Notice: Subject to any disclaimer, the term of this patent is extended or adjusted under 35 U.S.C. 154(b) by 240 days.

(21) Appl. No.: 15/319,163

(22) PCT Filed: Jun. 23, 2015

(86) PCT No.: PCT/JP2015/068094
§ 371 (c)(1),
(2) Date: Dec. 15, 2016

(87) PCT Pub. No.: WO2015/199097
PCT Pub. Date: Dec. 30, 2015

(65) Prior Publication Data
US 2017/0128430 A1  May 11, 2017

(30) Foreign Application Priority Data

Jun. 24, 2014 (JP) ................. 2014-129670
Jun. 24, 2014 (JP) ................. 2014-129672
Mar. 4, 2015 (JP) ................. 2015-042637
Mar. 4, 2015 (JP) ................. 2015-042638

(51) Int. Cl.
A61K 36/00 (2006.01)
A61K 36/752 (2006.01)
A61K 31/4439 (2006.01)
A61K 31/4725 (2006.01)
A61K 36/53 (2006.01)
A61K 31/202 (2006.01)
A61K 36/534 (2006.01)
A61K 36/61 (2006.01)
A61K 36/54 (2006.01)
A61K 36/63 (2006.01)
A61K 36/532 (2006.01)
A61K 36/484 (2006.01)
A61K 45/06 (2006.01)

(52) U.S. Cl.
CPC ........ A61K 31/4439 (2013.01); A61K 31/202 (2013.01); A61K 31/4725 (2013.01); A61K 36/00 (2013.01); A61K 36/484 (2013.01); A61K 36/53 (2013.01); A61K 36/532 (2013.01); A61K 36/534 (2013.01); A61K 36/54 (2013.01); A61K 36/61 (2013.01); A61K 36/63 (2013.01); A61K 36/752 (2013.01); A61K 45/06 (2013.01)

(58) Field of Classification Search
None
See application file for complete search history.

(56) References Cited

U.S. PATENT DOCUMENTS

| 5,817,689 A | 10/1998 | Kato et al. |
| 2004/0106543 A1* | 6/2004 | Smith ............ A61K 38/28 514/5.9 |
| 2007/0129339 A1* | 6/2007 | Surwit ............ A61K 31/549 514/151 |
| 2010/0292277 A1 | 11/2010 | Von Borstel et al. |

FOREIGN PATENT DOCUMENTS

| JP | H10-033178 A | 2/1998 |
| JP | 2006-056881 A | 3/2006 |
| JP | 2008-509213 A | 3/2008 |
| JP | 2009-215184 A | 9/2009 |
| JP | 2009-532372 A | 9/2009 |
| WO | WO 96/16938 A1 | 6/1996 |
| WO | WO 2006/016357 A1 | 2/2006 |

OTHER PUBLICATIONS

Grigsby, J., et al., (A possible role acrolein in diabetic retinopathy; involvement of VEGF/TGFb signaling pathway of the reinal pigment epithelium in hyperglycemia, Curr Eye Res., 2012, 37 (aa), 1045-53) (also see submiited document within the IDS) (Year: 2012).*
Ohno, H. et al., "PPARγ agonists induce a white-to-brown fat conversion through stabilization of PRDM16 protein," Cell Metab. Mar. 7, 2012;15(3):395-404. doi: 10.1016/j.cmet.2012.01.019.
International Search Report (ISR) for PCT/JP2015/068094; I.A. fd: Jun. 23, 2015, dated Sep. 1, 2015 from the Japan Patent Office, Tokyo, Japan.
International Preliminary Report on Patentability (IPRP), Chapter I of the Patent Cooperation Treaty, including the Written Opinion for PCT/JP2015/068094; I.A. fd: Jun. 23, 2015, dated Dec. 27, 2016, by the International Bureau of WIPO, Geneva, Switzerland.
Seale, P. et al., "Brown fat in humans: turning up the heat on obesity," Diabetes. Jul. 2009;58(7):1482-4. doi: 10.2337/db09-0622, American Diabetes Association, Alexandria, VA.
Lehrke, M. et al., "The many faces of PPARγ," Cell. Dec. 16, 2005;123(6):993-9, Elsevier Inc., USA.
Watkins, SM et al., "Lipid metabolome-wide effects of the PPARγ agonist rosiglitazone," J Lipid Res. Nov. 2002;43(11):1809-17, Lipid Research, Inc., Memphis, TN.

(Continued)

Primary Examiner — Michael Barker
(74) Attorney, Agent, or Firm — Sterne, Kessler, Goldstein & Fox P.L.L.C.

(57) ABSTRACT

It is intended to provide a drug, a quasi-drug, a dermatological preparation for external use, or a material to be contained to drugs, quasi-drugs, dermatological preparations for external use, food products, or the like which has an excellent UCP-1 expression-promoting action and promotes conversion of adipose to brown adipose (browning). The present invention provides a UCP-1 expression promoter comprising a PPARγ activator and a Smad3 inhibitor in combination. The present invention also provides a UCP-1 expression promoter comprising a PPARγ activator, a Smad3 inhibitor, and a β3 adrenaline receptor activator or a TGR5 activator in combination.

7 Claims, 14 Drawing Sheets

(56) References Cited

OTHER PUBLICATIONS

Jinnin, M. et al., "Characterization of SIS3, a novel specific inhibitor of Smad3, and its effect on transforming growth factor-β1-induced extracellular matrix expression," Mol Pharmacol. Feb. 2006;69(2):597-607. Epub Nov. 15, 2005, Am. Soc. for Pharmacol. and Exper. Therapeutics, Bethesda, MD.

Yadav, H. et al., "Protection from obesity and diabetes by blockade of TGF-β/Smad3 signaling," Cell Metab. Jul. 6, 2011;14(1):67-79. doi: 10.1016/j.cmet.2011.04.013, Cell Press, Cambridge, MA.

Tan, CK et al., "Smad3 deficiency in mice protects against insulin resistance and obesity induced by a high-fat diet," Diabetes. Feb. 2011;60(2):464-76. doi: 10.2337/db10-0801, American Diabetes Assoc, Alexandria, VA.

Bloom, JD et al., "Disodium (R,R)-5-[2-[[2-(3-chlorophenyl)-2-hydroxyethyl]-amino] propyl]-1,3-benzodioxole-2,2-dicarboxylate (CL316,243). A potent β-adrenergic agonist virtually specific for $\beta_3$ receptors. A promising antidiabetic and antiobesity agent," J Med Chem. Aug. 7, 1992;35(16):3081-4, Amer. Chem. Soc., Washington, DC.

Saito, M., "Roles of UCP in the regulation of energy expenditure," $124^{th}$ Symposium of the Japanese Association of Medical Sciences, Aug. 29-31, 2003, Hakone City Kanagawa, Japan, pp. 62-7, Japanese Assoc Med Sciences, Tokyo, Japan.

Ishii, S., "Bile acids and their pathophysiological role in metabolic disorders," Folia pharmacologica Japonica (Nihon Yakurigaku Zasshi). Nov. 2010;136(5):265-9, Nippon Yakuri Gakkai, Tokyo, Japan.

Tan, CK et al., "Getting 'Smad' about obesity and diabetes," Nutr Diabetes. Mar. 5, 2012;2:e29. doi: 10.1038/nutd.2012.1, Macmillan Publishers Limited, London, England.

Siriwardhana, N et al., "Modulation of adipose tissue inflammation by bioactive food compounds," J Nutr Biochem. Apr. 2013;24(4):613-23. doi: 1.1016/j.jnutbio.2012.12.013, Elsevier, New York, NY.

Grigsky, J et al., "A possible role of acrolein in diabetic retinopathy: involvement of a VEGF/TGFβ signaling pathway of the retinal pigment epithelium in hyperglycemia," HHS Public Access author manuscript, available in PMC Jun. 26, 2015, published in final form as Curr Eye Res. Nov. 2013;37(11):1045-53. doi: 10.3109/02713683. 2012.713152. Epub Aug. 20, 2012, Informa Healthcare, London, England.

Chuang, H-Y et al., "Hydrolysable tannins of tropical almond show antifibrotic effects in TGF-β1-induced hepatic stellate cells," J Sci Food Agric. Dec. 2011;91(15):2777-84. doi: 10.1002/jsfa.4521. Epub Jul. 1, 2011, John Wiley & Sons, Chichester, West Sussex, England.

Zhao, J et al., "$a\alpha_1$-Adrenergic stimulation potentiates the thermogenic action of $\beta_3$-adrenoreceptor-generated cAMP in brown fat cells," J Biol Chem. Dec. 26, 1997;272(52):32847-56, American Society for Biochemistry and Molecular Biology, Baltimore, MD.

Ohsaka, Y. et al., "Suppression of insulin-stimulated phosphatidylinositol 3-kinase activity by the $\beta_3$-adrenoceptor agonist CL316243 in rat adipocytes," FEBS Lett. Feb. 3, 1997;402(2-3):246-50, Federation of European Biochemical Societies, Amsterdam, North Holland.

* cited by examiner

[Figure 1]
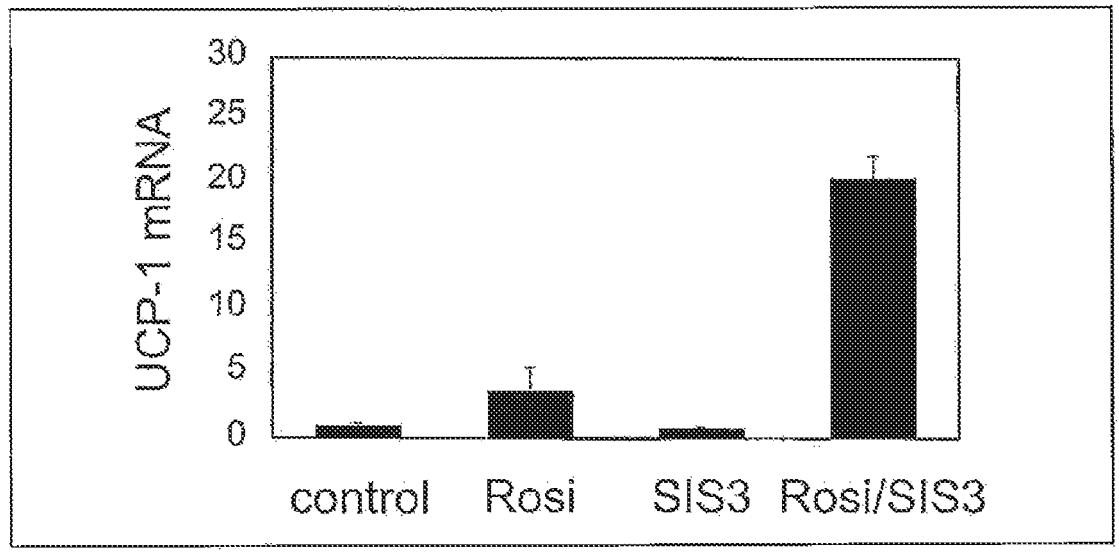
[Figure 2]
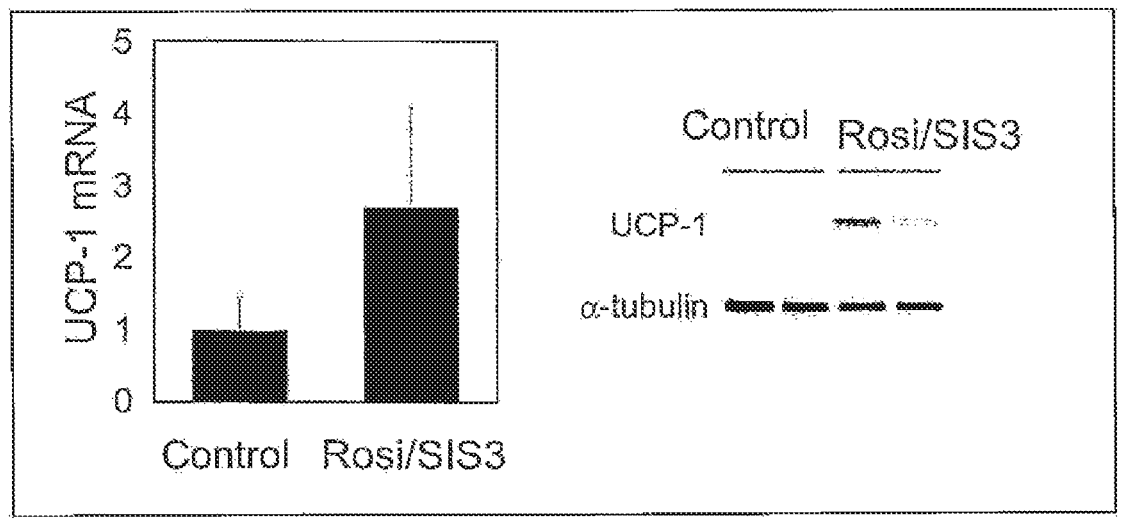

[Figure 3]
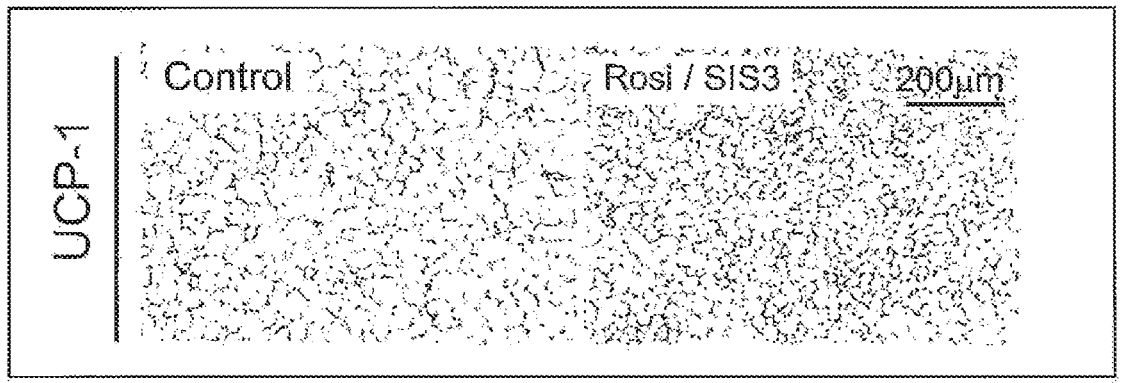
[Figure 4]
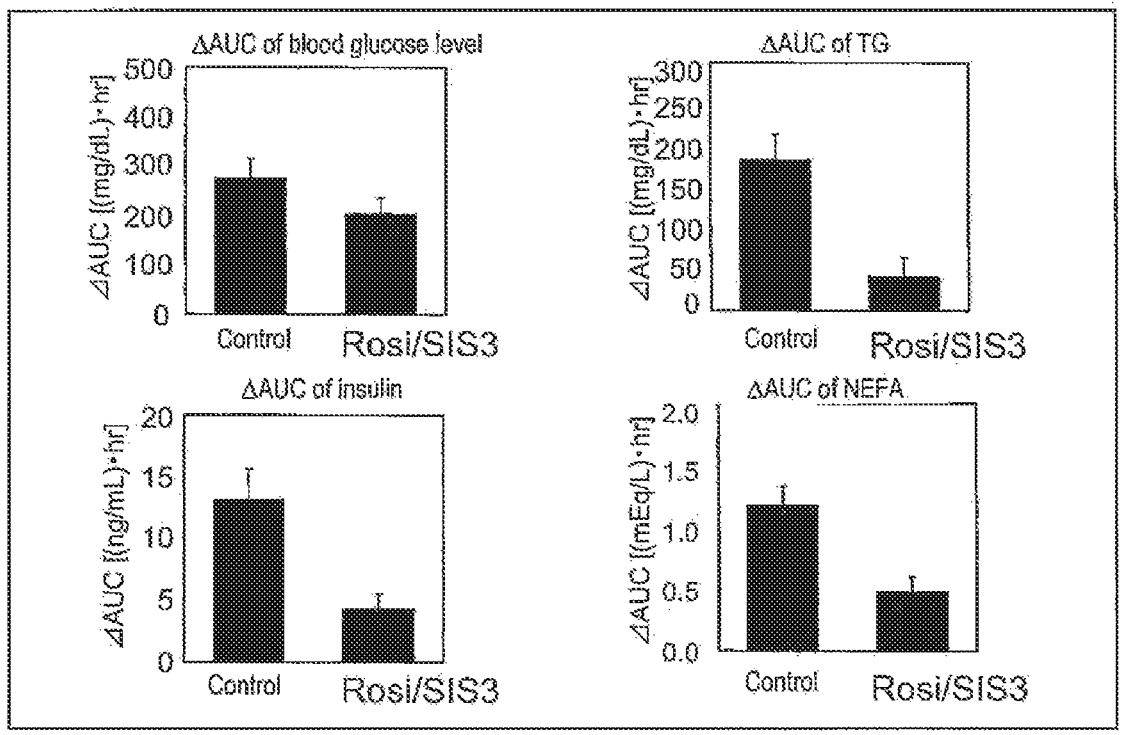

[Figure 5]
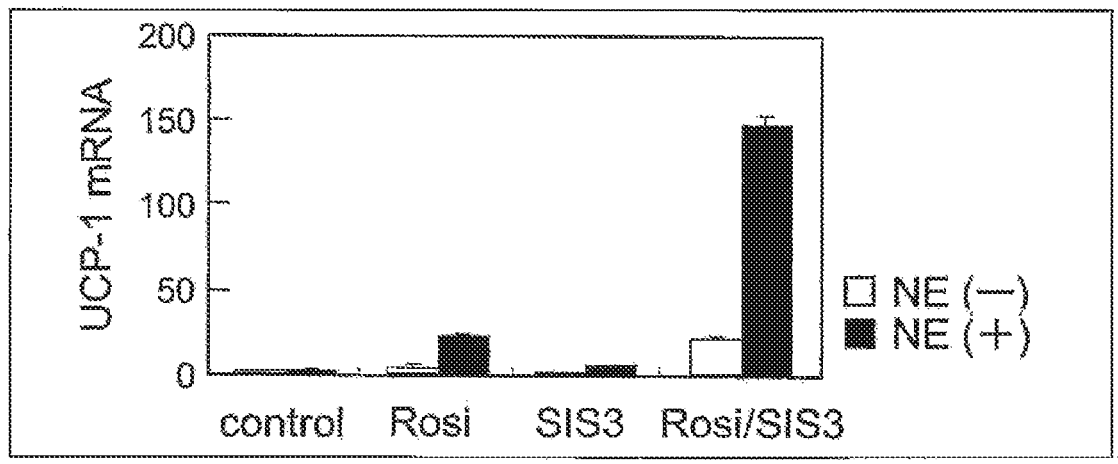
[Figure 6]
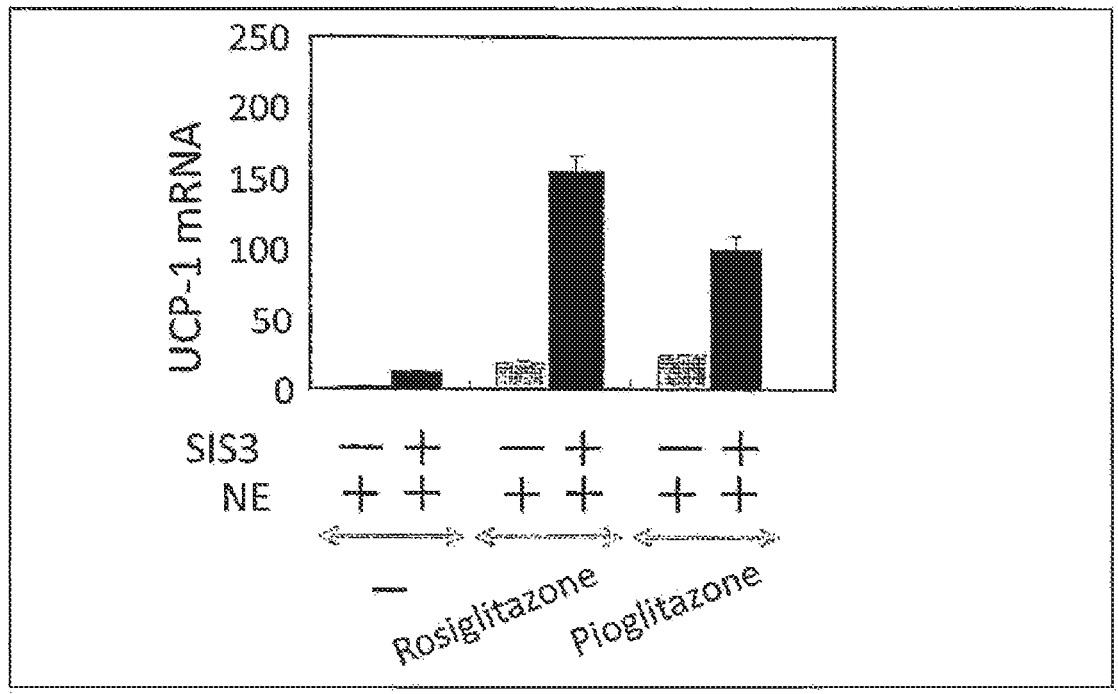

[Figure 7]
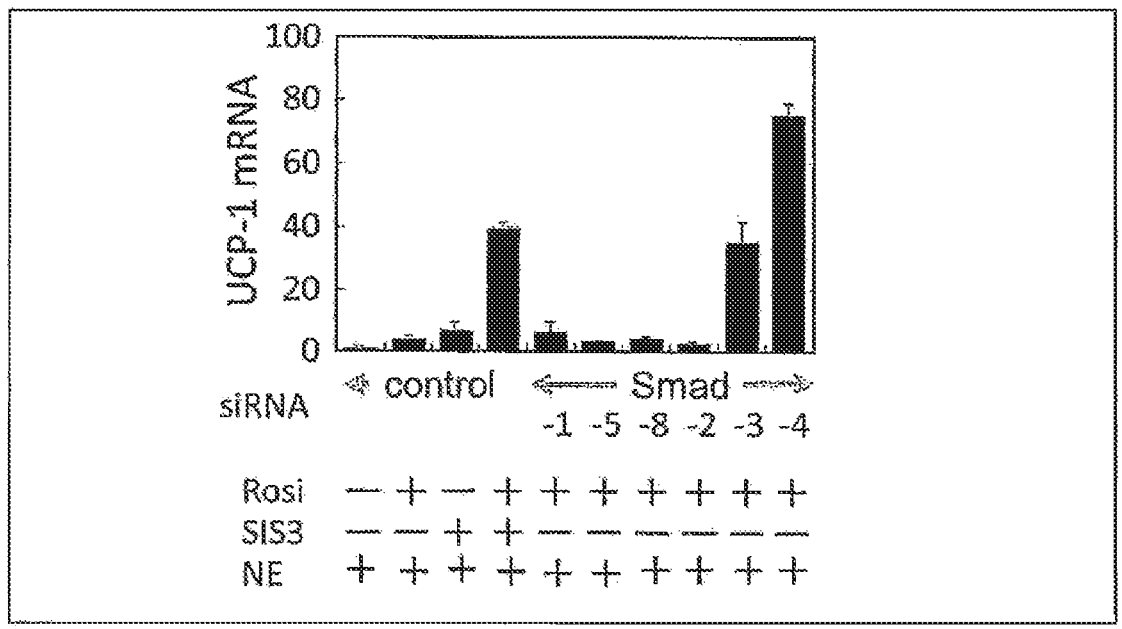
[Figure 8]
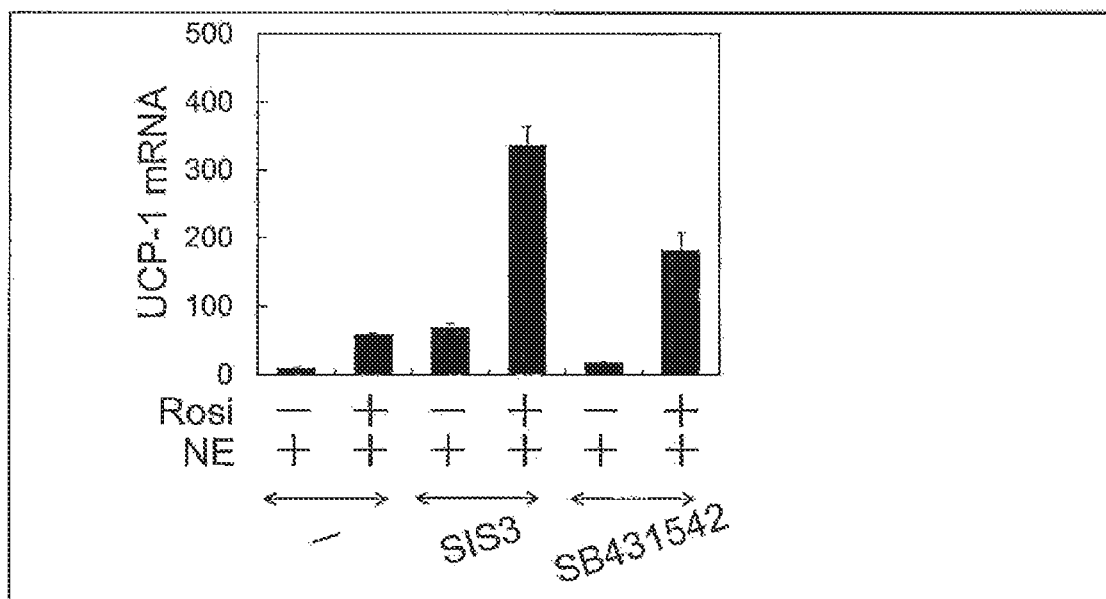

[Figure 9]
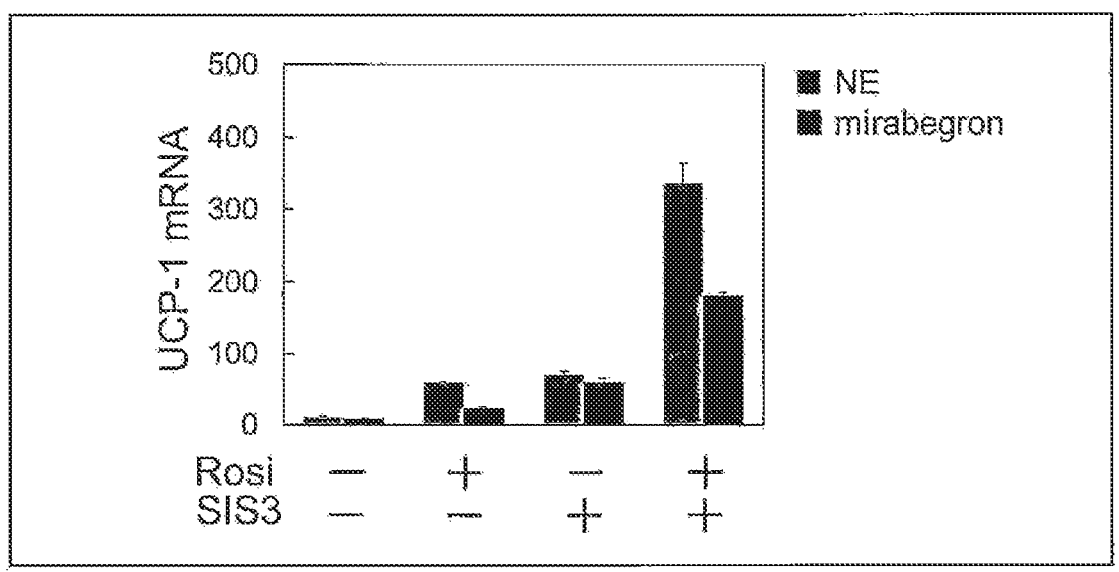

[Figure 10]
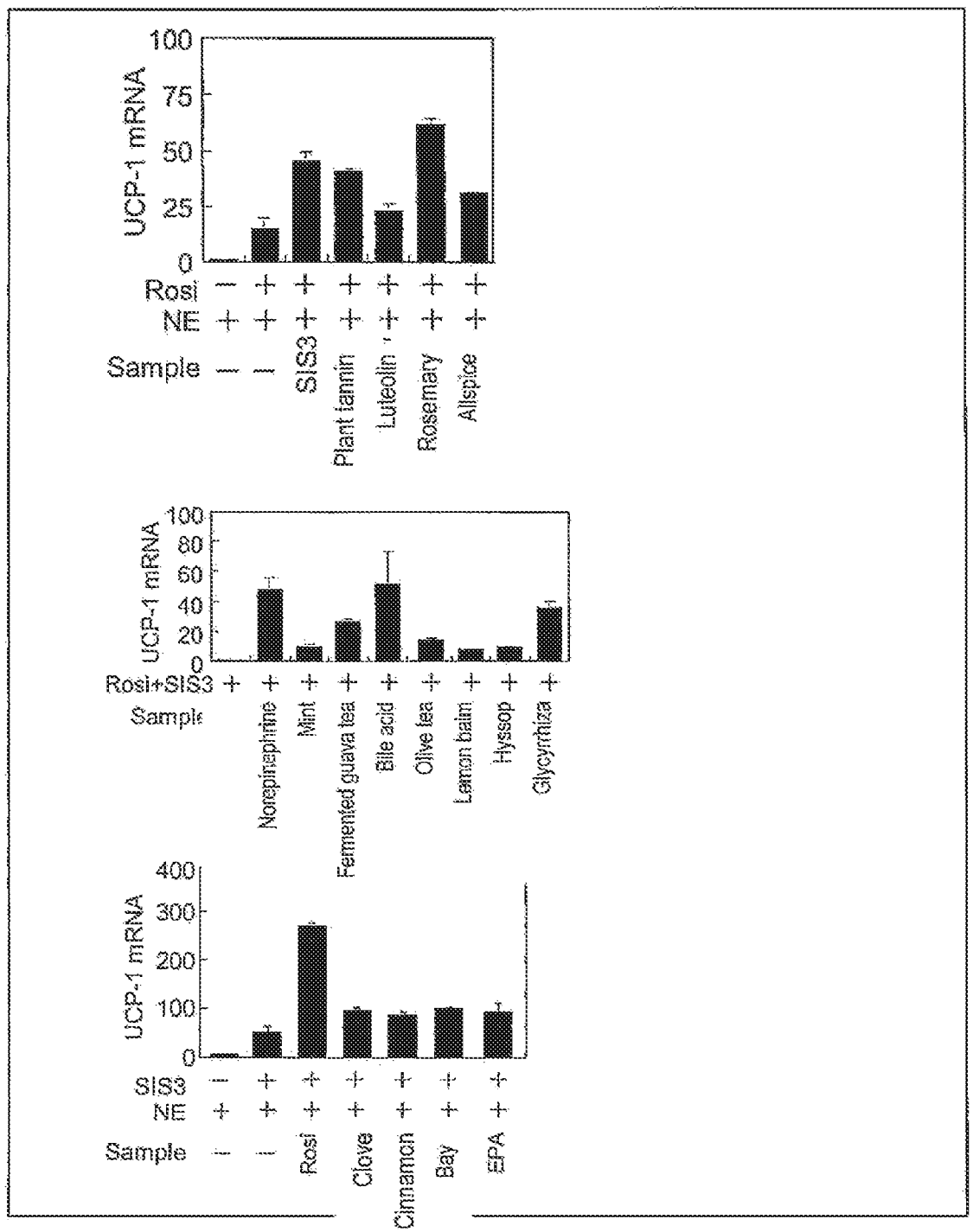

[Figure 11]
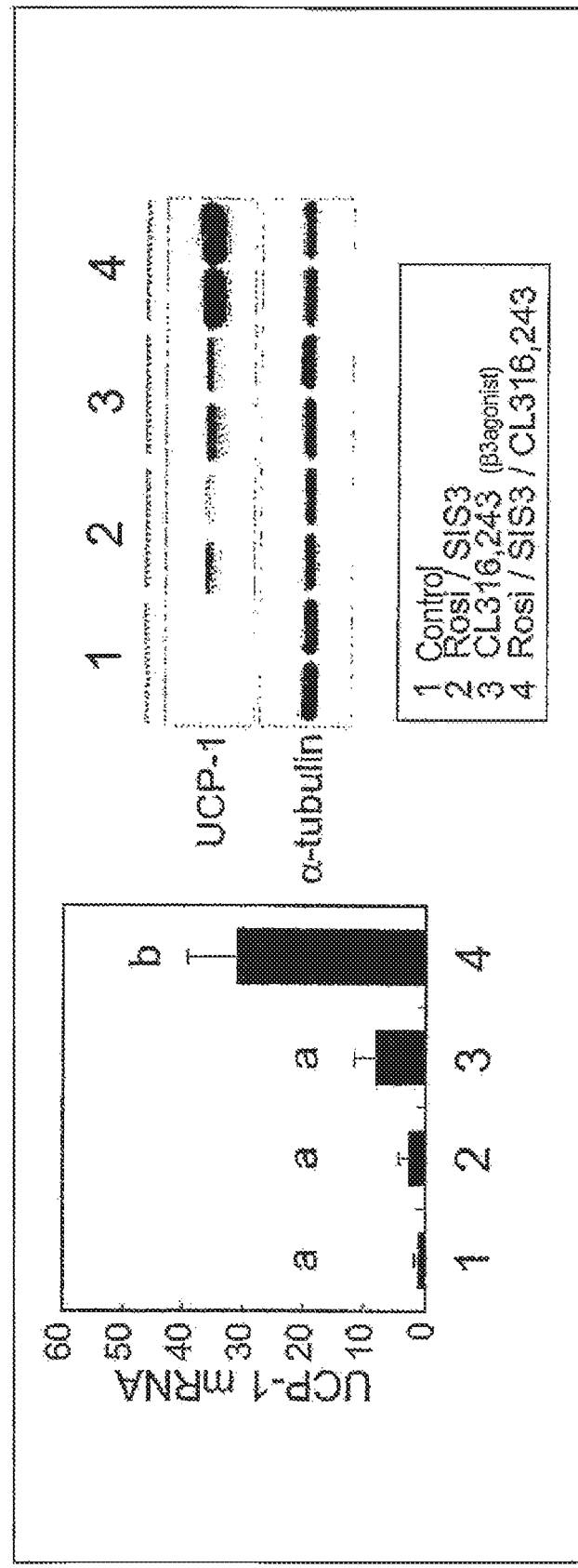

[Figure 12]
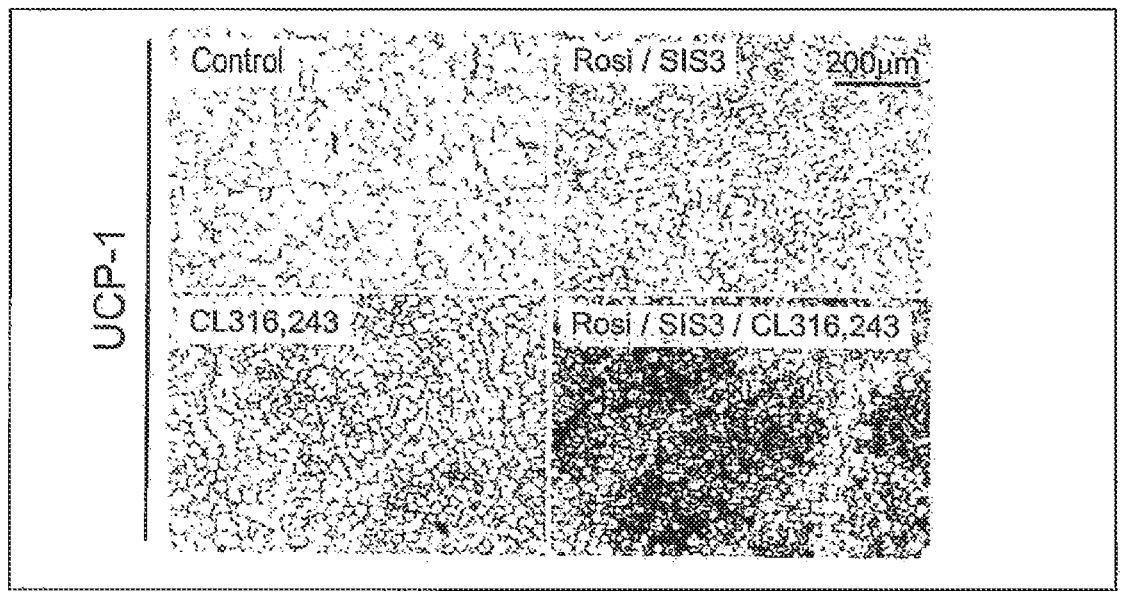
[Figure 13]
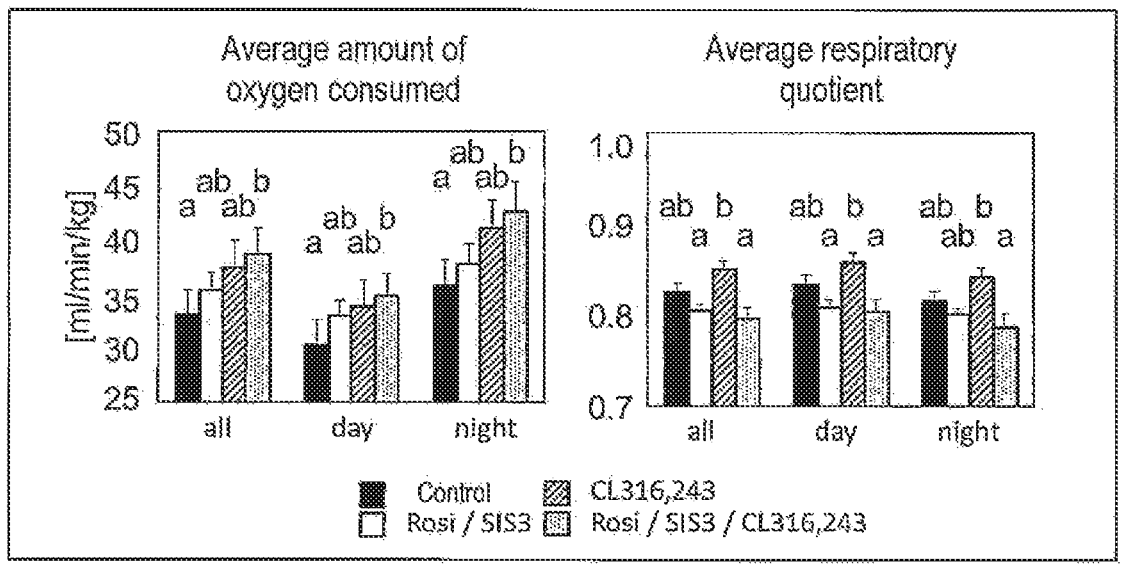

[Figure 14]
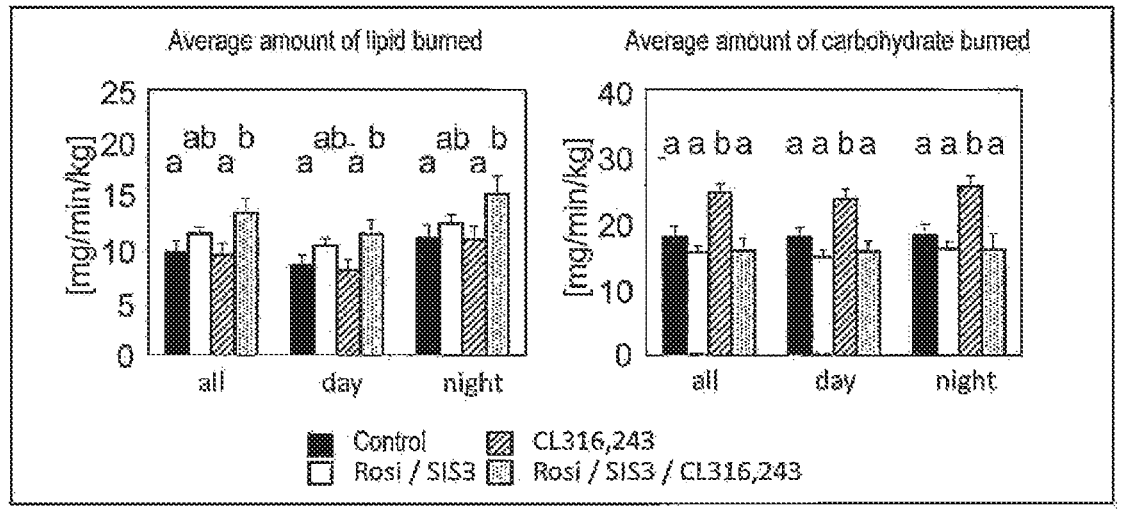
[Figure 15]
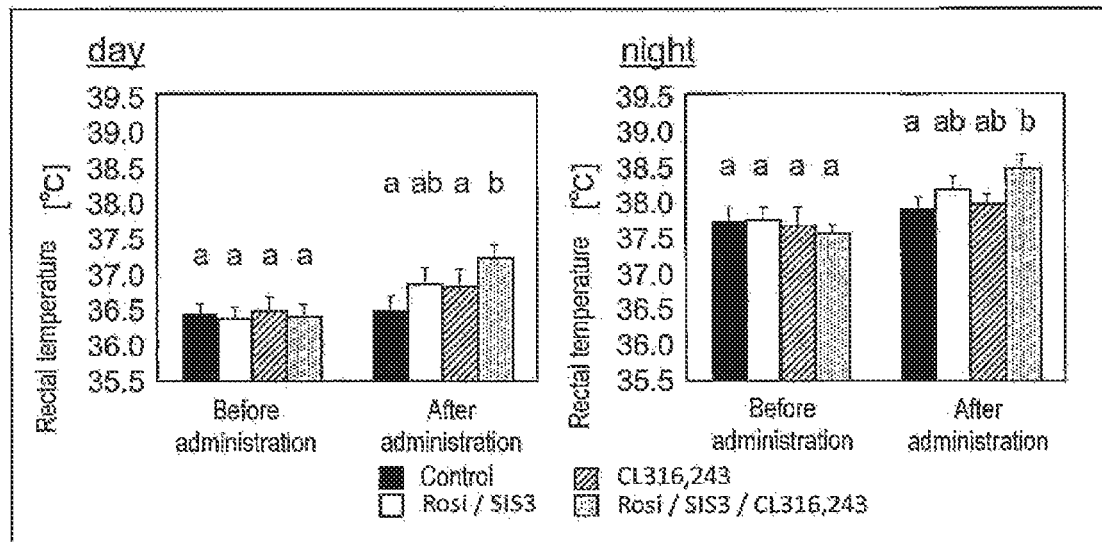

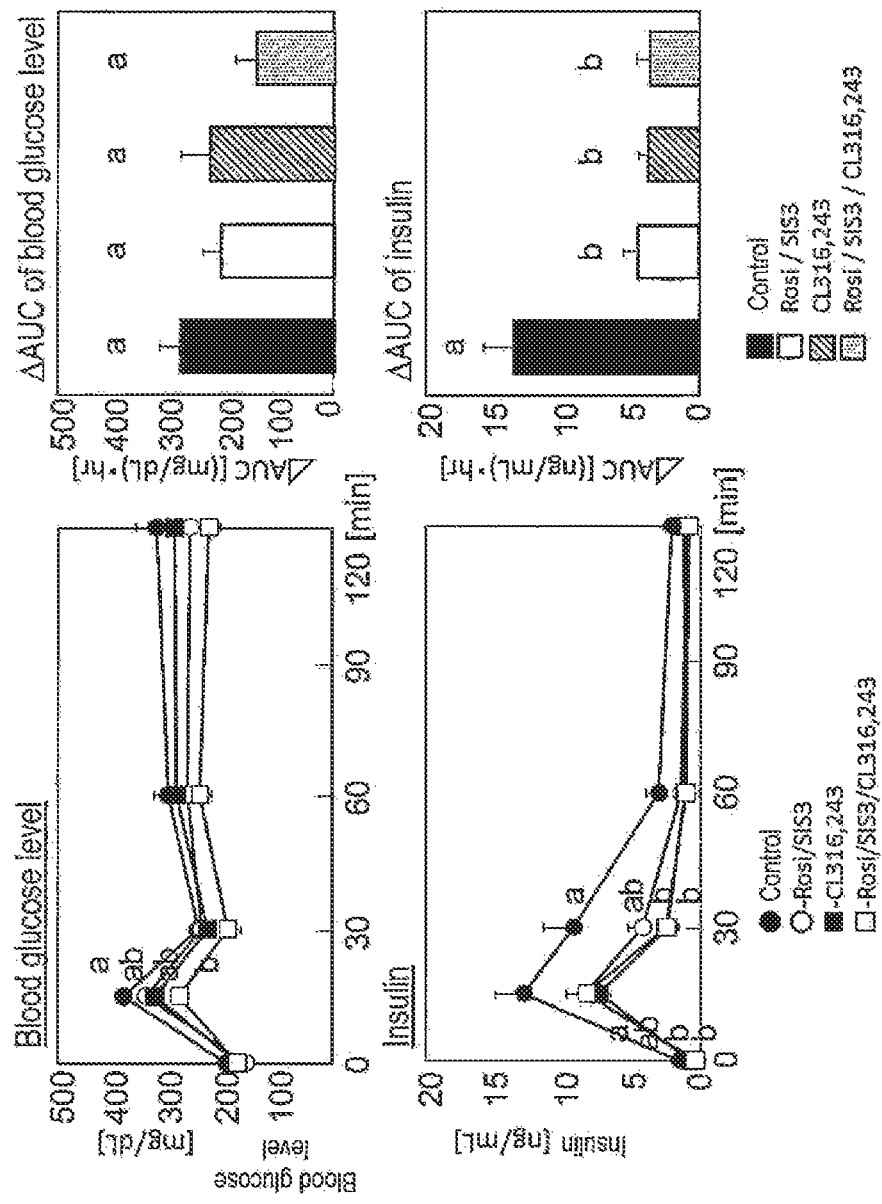
[Figure 16]

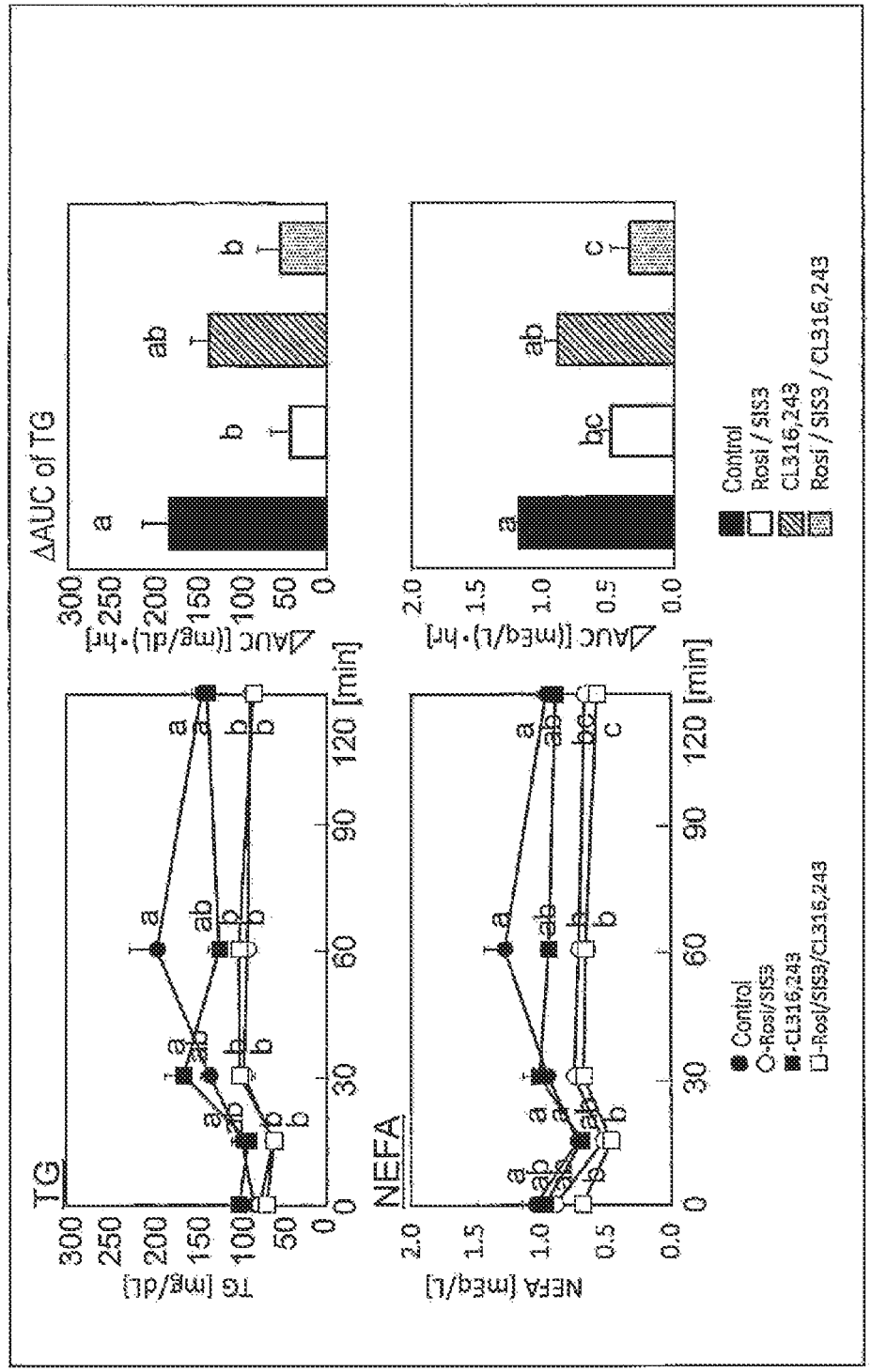
[Figure 17]

[Figure 18]
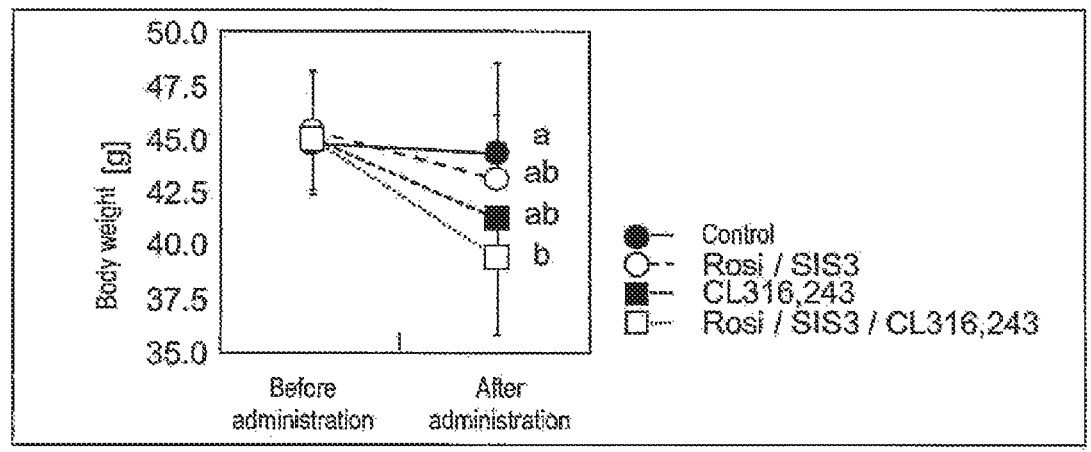
[Figure 19]
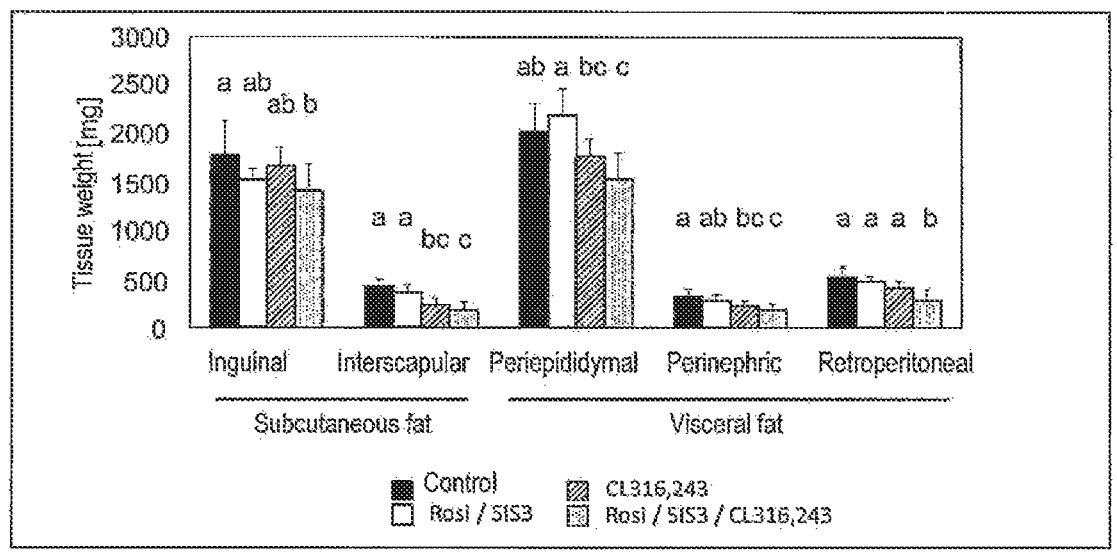

[Figure 20]
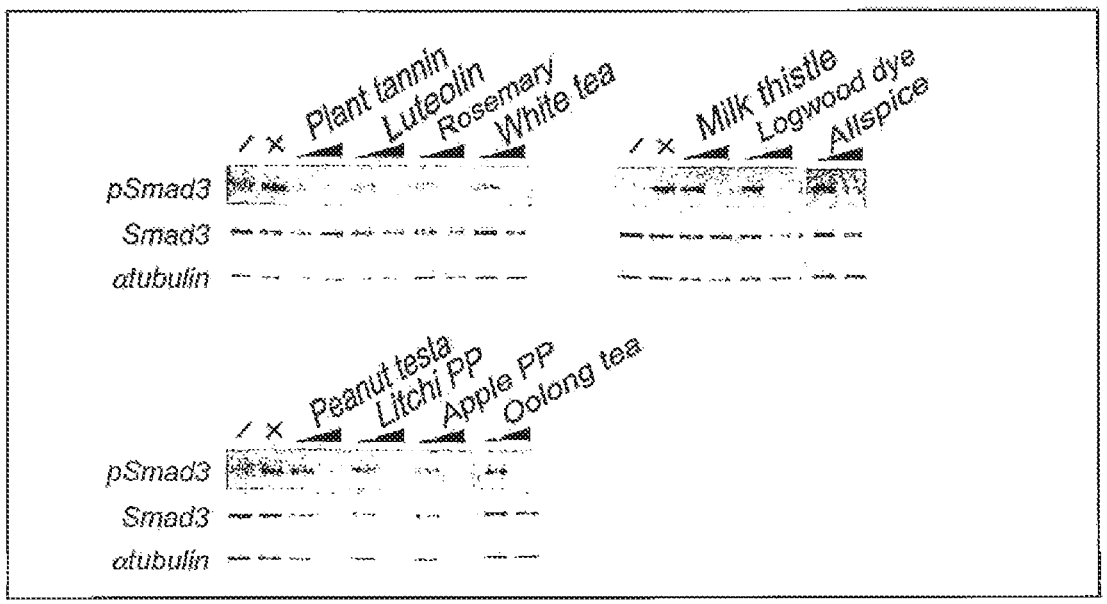
[Figure 21]
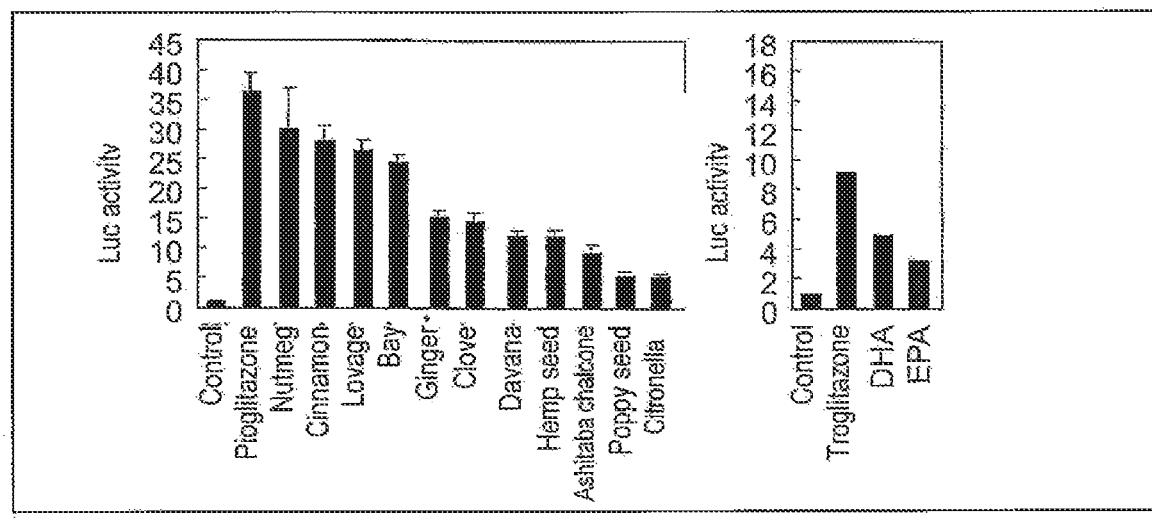

[Figure 22]
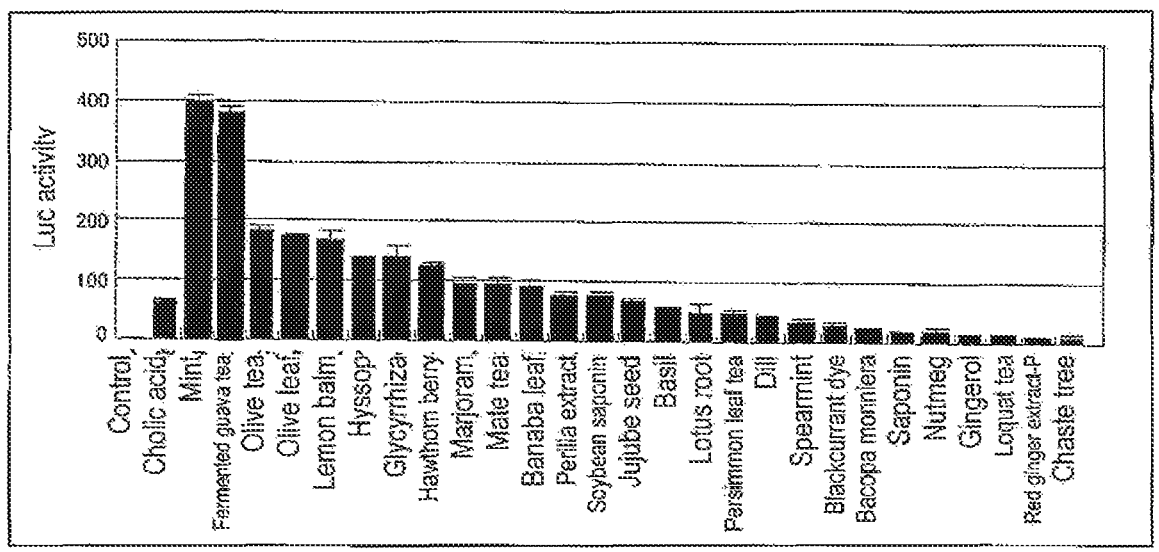

UCP-1 EXPRESSION PROMOTER

FIELD OF THE INVENTION

The present invention relates to a UCP-1 expression promoter which promotes a conversion to brown adipose and promotes the expression of UCP-1.

BACKGROUND OF THE INVENTION

Heretofore, adipose has been broadly classified into white adipose and brown adipose. The white adipose is an organ which stores excessive energy in the form of unilocular lipid droplets in white adipose cells and releases fatty acids according to a nutrition status. Brown adipose cells found in a large amount in the brown adipose have many mitochondria, specifically express a high level of UCP-1 (uncoupling protein-1), and have the property of dissipating energy in the form of heat.

UCP has the function of uncoupling oxidative phosphorylation reaction in the mitochondrial inner membrane and dissipating energy as heat. Recent studies have revealed that the increased expression level of UCP-1, which is typical UCP in brown adipose cells, promotes heat production and consequently increases the consumption of carbohydrate or lipid energy, leading to the inhibition of the fat accumulation, obesity, and diabetes mellitus. Thus, conversion to brown adipose has received attention from the viewpoint of the prevention or amelioration of obesity or metabolic syndrome (Non Patent Literature 1).

Meanwhile, PPARγ (peroxisome proliferator-activated receptor γ), one kind of peroxisome proliferator-activated receptors, is known to prevent or ameliorate diabetes mellitus or insulin resistance through its activation (Non Patent Literature 2). For example, a PPARγ activator pioglitazone or rosiglitazone is utilized as a drug for type 2 diabetes (Non Patent Literature 3).

On the other hand, the Smad family is an intracellular signaling factor which is phosphorylated by stimulation of a TGF-β (transforming growth factor-β) family molecule to transduce the signals thereof to the nucleus. A Smad3-specific Inhibitor SIS3 (specific inhibitor of Smad3) is expected as an agent for prevention or amelioration of tissue fibrosis caused by TGF-β (Non Patent Literature 4). In recent, years, Smad3-deficient mice have shown resistance to dietary obesity and diabetes mellitus, suggesting the possibility that the TGF-β/Smad3 signaling pathway is involved in glucose and energy homeostasis. Thus, the application of a TGF-β control method to prevention or amelioration of obesity and diabetes mellitus has been studied (Non Patent Literature 5). On the other hand, it has also been reported that serum triglyceride levels are rather increased in Smad3-deficient mice, and insulin is also increased (Non Patent Literature 6).

β Adrenaline receptors include 3 subtypes which are classified as β1, β2, and β3. For example, the β3 adrenaline receptor is known to exist mainly in adipose cells, the brain, the gallbladder, the prostate, the bladder, and the intestinal tract and additionally exist in the liver, the stomach, etc. It has been reported as to the β3 adrenaline receptor that stimulation mediated by this receptor causes a lipolysis-promoting action, a heat production-promoting action, a hypoglycemic action, an antihyperlipidemic action, an intestinal motility-inhibiting action, a glucose uptake-promoting action, an antidepressive action, and the like (Patent Literature 1 and Non Patent Literatures 7 and 8).

TGR5 has been reported to exist mainly in skeletal muscle and brown adipose cells and have effects of promoting heat production in adipose tissues and improving energy metabolism by a function of, for example, bile acid as an endogenous ligand of TGR5 (Non Patent Literature 9).

[Patent Literature 1] JP-A-10-33178
[Non Patent Literature 1] Patrick Seale et al., DIABETES, VOL. 58, 1482-1484, 2009
[Non Patent Literature 2] Michael Lehrke et al., Cell 123, 993-999, 2005
[Non Patent Literature 3] Steven M. Watkins et al., Journal of Lipid Research Volume 43, 1809-1817, 2002
[Non Patent Literature 4] Masatoshi Jinnin et al., Mol Pharmacol 63, 597-607, 2006
[Non Patent Literature 5] Hariom Yadav et al., Cell Metabolism 14, 67-79, 2011
[Non Patent Literature 6] Chek Kun Tan et al., Diabetes, 60, 464-476, 2011
[Non Patent Literature 7] David C. Humber et al., J. Med. Chem. 35, 3081-3084, 1992
[Non Patent Literature 8] Masayuki Saito, "Roles of UCP in the regulation of energy expenditure", the 124th Symposium of the Japanese Association of Medical Sciences, 62-70, 2003
[Non Patent Literature 9] Shinichi Ishii, "Bile acids and their pathophysiological role in metabolic disorders", Folia, Pharmacol. Jpn., vol. 136, No. 5, November 2010

SUMMARY OF THE INVENTION

The present invention relates to the following (1) to (20):

(1) A UCP-1 expression promoter comprising a PPARγ activator and a Smad3 inhibitor in combination.

(2) A promoter of conversion to brown adipose comprising a PPARγ activator and a Smad3 inhibitor in combination.

(3) An energy consumption promoter comprising a PPARγ activator and a Smad3 inhibitor in combination.

(4) A body fat accumulation inhibitor comprising a PPARγ activator and a Smad3 inhibitor in combination.

(5) A preventive or ameliorative agent for obesity comprising a PPARγ activator and a Smad3 inhibitor in combination.

(6) A preventive or ameliorative agent for diabetes mellitus comprising a PPARγ activator and a Smad3 inhibitor in combination.

(7) A preventive or ameliorative agent for hyperlipidemia comprising a PPARγ activator and a Smad3 inhibitor in combination.

(8) A method for promoting UCP-1 expression, a method for promoting conversion to brown adipose, a method for promoting energy consumption, a method for inhibiting body fat accumulation, a method for preventing or ameliorating obesity, a method for preventing or ameliorating diabetes mellitus, or a method for preventing or ameliorating hyperlipidemia, comprising ingesting or administering a PPARγ activator and a Smad3 inhibitor in combination, or combining ingestion or administration of a PPARγ activator and a treatment for inhibiting Smad3.

(9) A UCP-1 expression promoter comprising a PPARγ activator, a Smad3 inhibitor, and a β3 adrenaline receptor activator or a TGR5 activator in combination.

(10) A promoter of conversion to brown adipose comprising a PPARγ activator, a Smad3 inhibitor, and a β3 adrenaline receptor activator or a TGR5 activator in combination.

(11) An energy consumption promoter comprising a PPARγ activator, a Smad3 inhibitor, and a β3 adrenaline receptor activator or a TGR5 activator in combination.

(12) A body fat accumulation inhibitor comprising a PPARγ activator, a Smad3 inhibitor, and a β3 adrenaline receptor activator or a TGR5 activator in combination.

(13) A preventive, or ameliorative agent for obesity comprising a PPARγ activator, a Smad3 inhibitor, and a β3 adrenaline receptor activator or a TGR5 activator in combination.

(14) A preventive or ameliorative agent for diabetes mellitus comprising a PPARγ activator, a Smad3 inhibitor, and a β3 adrenaline receptor activator or a TGR5 activator in combination.

(15) A preventive or ameliorative agent for hyperlipidemia comprising a PPARγ activator, a Smad3 inhibitor, and a β3 adrenaline receptor activator or a TGR5 activator in combination.

(16) A lipid burning promoter comprising a PPARγ activator, a Smad3 inhibitor, and a β3 adrenaline receptor activator or a TGR5 activator in combination.

(17) A carbohydrate metabolism-improving agent comprising a PPARγ activator, a Smad3 inhibitor, and a β3 adrenaline receptor activator or a TGR5 activator in combination.

(18) A lipid metabolism-improving agent comprising a PPARγ activator, a Smad3 inhibitor, and a β3 adrenaline receptor activator or a TGR5 activator in combination.

(19) An adiponectin production promoter comprising a PPARγ activator, a Smad3 inhibitor, and a β3 adrenaline receptor activator or a TGR5 activator in combination.

(20) A method for promoting UCP-1 expression, a method for promoting conversion to brown adipose, a method for promoting energy consumption, a method for inhibiting body fat accumulation, a method for preventing or ameliorating obesity, a method for preventing or ameliorating diabetes mellitus, a method for preventing or ameliorating hyperlipidemia, a method for promoting lipid burning, a method for improving carbohydrate metabolism, a method for improving lipid metabolism, or a method for promoting adiponectin production, comprising combining ingestion or administration of a PPARγ activator, ingestion or administration of a Smad3 inhibitor or a treatment for inhibiting Smad3, and ingestion or administration of a β3 adrenaline receptor activator or a TGR5 activator or a treatment for activating β3 adrenaline receptor or TGR5.

BRIEF DESCRIPTION OF DRAWINGS

FIG. 1 is a graph showing a UCP-1 expression level (in vitro).

FIG. 2 is a graph showing a UCP-1 expression level (in vivo). Left diagram: results of quantitative PCR, and right diagram: results of Western blotting.

FIG. 3 is a microscope photograph showing the immunohistochemical staining image of UCP-1 in inguinal subcutaneous fat.

FIG. 4 is a graph showing carbohydrate metabolism- and lipid metabolism-improving effects. Upper left diagram: ΔAUC of a blood glucose level, lower left diagram: ΔAUC of insulin, upper right diagram: ΔAUC of triglyceride, and lower right diagram: ΔAUC of NEFA.

FIG. 5 is a graph showing a UCP-1 expression level (in vitro).

FIG. 6 is a graph showing a UCP-1 expression level (in vitro) on the basis of the presence or absence of a PPARγ activator.

FIG. 7 is a graph showing a UCP-1 expression level (in vitro) in the presence or absence of a Smad3 inhibitor and siRNA.

FIG. 8 is a graph showing a UCP-1 expression level (in vitro) in the presence or absence of a Smad3 inhibitor.

FIG. 9 is a graph showing a UCP-1 expression level (in vitro) in the presence or absence of a β3 adrenaline receptor activator.

FIG. 10 is a graph showing a UCP-1 expression level (in vitro).

FIG. 11 is a graph showing a UCP-1 expression level (in vivo). Left diagram: results of quantitative PCR, and right diagram: results of Western blotting.

FIG. 12 is a microscope photograph showing the immunohistochemical staining image of UCP-1 in inguinal subcutaneous fat.

FIG. 13 is a graph showing results of measuring the amount of oxygen consumed and a respiratory quotient. Left diagram: average amount of oxygen consumed, and right diagram: average respiratory quotient. All: whole day, Day: light period, and Night: dark period.

FIG. 14 is a graph showing results of measuring the amount of lipid burned and the amount of carbohydrate burned. Left diagram: average amount of lipid burned, and right diagram: average amount of carbohydrate burned. All: whole day, Day: light period, and Night: dark period.

FIG. 15 is a graph showing results of measuring a rectal temperature. Left diagram: light period, and right diagram: dark period.

FIG. 16 is a graph showing results of measuring carbohydrate metabolism. Upper left diagram: blood glucose level, upper right diagram: ΔAUC of a blood glucose level, lower left diagram: insulin, and lower right diagram: ΔAUC of insulin.

FIG. 17 is a graph showing results of measuring lipid metabolism. Upper left diagram: triglyceride, upper right diagram: ΔAUC of triglyceride, lower left diagram: NEFA, lower right diagram: ΔAUC of NEFA FIG. 18 is a graph showing results of measuring a rat body weight.

FIG. 19 is a graph showing results of measuring a rat adipose tissue weight.

FIG. 20 is a diagram showing a TGF-β stimulation-responsive Smad3 hyperphosphorylation-inhibiting effect. (Left lanes; low-concentration sample, and right lanes; high-concentration samples)

FIG. 21 is a diagram showing a PPARγ-activating effect.

FIG. 22 is a diagram showing TGR5-activating effect.

DETAILED DESCRIPTION OF THE INVENTION

The present invention relates to a provision of a drug, a quasi-drug, a dermatological preparation for external use, or a material to be contained to drugs, quasi-drugs, dermatological preparations for external use, food products, or the like, which has an excellent UCP-1 expression-promoting effect and promotes conversion to brown adipose (also referred to as browning).

The present inventors have conducted studies to solve the problem mentioned above and consequently found that a PPARγ activator and a Smad3 inhibitor used in combination, or a PPARγ activator, a Smad3 inhibitor, and a β3 adrenaline receptor activator or a TGR5 activator used in combination significantly promote the expression of UCP-1 and promote conversion to brown adipose, and the combinations are useful as a material for drugs, quasi-drugs, dermatological preparations for external use, food products, or the like capable of exerting each effect of promoting energy consumption, inhibiting body fat accumulation, preventing or ameliorating obesity, preventing or ameliorating hyperlipidemia, preventing or ameliorating diabetes mellitus, promoting lipid burning, improving carbohydrate metabolism, and improving lipid metabolism.

The present invention can provide a drug, a quasi-drug, or a material for use in drugs, quasi-drugs, or food products, and a method which have excellent actions of promoting the UCP-1 expression and converting to brown adipose and are useful for the promotion of energy consumption, the inhibition of body fat accumulation, the prevention or amelioration of obesity, the prevention or amelioration of diabetes mellitus, the prevention or amelioration of hyperlipidemia, the promotion of lipid burning, the improvement of carbohydrate metabolism, the improvement of lipid metabolism, the promotion of adiponectin production, etc. Thus, the present invention, enables the promotion of the expression of UCP-1 and the conversion to brown adipose to achieve the promotion of energy consumption, the inhibition of body fat accumulation, the prevention or amelioration of obesity, the prevention or amelioration of diabetes mellitus, the prevention or amelioration of hyperlipidemia, the promotion of lipid burning, the improvement of carbohydrate metabolism, the improvement of lipid metabolism, and the promotion of adiponectin production.

The PPARγ activator used in the present invention is a generic name for a substance activating peroxisome proliferator-activated receptor (PPAR) γ and is called PPARγ activator, PPARγ ligand, or PPARγ agonist. A thiazolidine derivative known as a typical PPARγ activator is widely utilized as a drug for type 2 diabetes because this compound increases small adipose cells in adipose tissues and promotes the secretion of insulin-sensitive hormones such as adiponectin to improves insulin resistance.

Examples of the PPARγ activator include rosiglitazone (BRL49653) (J Biol Chem. 1995 Jun. 2; 270 (22): 12953-6) and pioglitazone (J Biol Chem. 1995 Jun. 2; 270 (22): 12953-6) represented by the structural formulae given below as well as netoglitazone (Bone. 2006 January; 38 (1): 74-84), darglitazone (J Pharmacol Exp Ther 305: 1173-1182), ciglitazone (J Biol Chem. 1995 Jun. 2; 270 (22): 12953-6), englitazone (J Biol Chem. 1995 Jun. 2; 270 (22): 12953-6), troglitazone (Eur J Biochem. 1996 Jul. 1; 239 (1): 1-7), rivoglitazone (Ann Pharmacother. 2013 June; 47 (6): 877-85), FK-614 (Metabolism. 2005 September; 54 (9): 1250-8), tesaglitazar (AZ-242) (Structure. 2001 August; 9 (8): 699-706), ragaglitazar (J Med Chem. 2001 Aug. 2; 44 (16): 2675-8), prostaglandin D2, J2, delta-12-prostaglandin J2, 15-deoxy-delta 12, 14-prostaglandin J2 (Cell. 1995 Dec. 1; 83 (5): 803-12), docosahexaenoic acid, eicosapentaenoic acid, linolenic acid, linoleic acid, arachidonic acid (Mol Endocrinol. 1997 June; 11 (6): 779-91), telmisartan (Acta Diabetol. 2005 April; 42 Suppl 1: S9-16), carnosic acid (Planta Med. 2006 August; 72 (10): 881-7), FMOC-L-leucine and derivatives thereof (JP-A-2004-501896), N-substituted indole having an aryloxyacetic acid substituent, dehydrodieugenol A, dehydrodieugenol B, magnolol, oleanolic acid, betulinic acid (JP-A-2005-97216), rosmarinic acid derivatives (JP-A-2006-273741), monoacylglycerol or derivatives thereof (JP-A-2008-106040), gingerols or derivatives thereof (JP-A-2008-285438), ginger (JP-A-2010-106001), diphenylethene derivatives (JP-A-2012-116799), hydroxylated derivatives of highly unsaturated fatty acids having a carbon chain length of 20 to 22 carbon atoms (International Publication No. WO 2002/102364), GW1929 (Diabetes. 1999 July; 48 (7): 1415-24), nTZDpa (Mol Endocrinol. 2003 April; 17 (4): 662-76), treatment products of lactic acid bacteria (International Publication No. WO 2013/084971), soy sauce cake (JP-A-2009-242382), and curcumin (Evid Based Complement Alternat Med. 2013; 2013: 470975. doi: 10.1155/2013/470975).

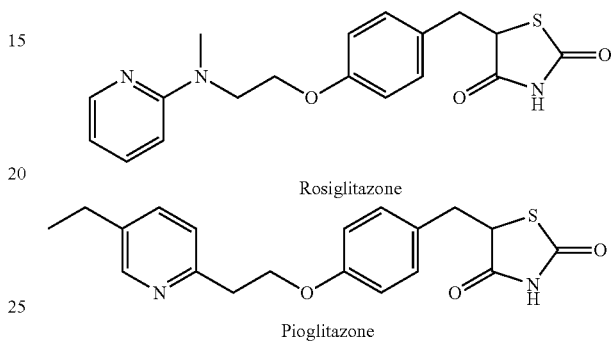

Rosiglitazone

Pioglitazone

As shown in Reference Examples described later, a ginger extract, a nutmeg extract, eicosapentaenoic acid (EPA), docosahexaenoic acid (DHA), a lovage extract, an elemi extract, a clove extract, a citronella extract, a bay extract, a cinnamon extract, a davana extract, a hemp seed extract, a poppy seed extract, and ashitaba chalcone have been confirmed to have a PPARγ-activating action, and ginger or an extract thereof, nutmeg or an extract thereof, eicosapentaenoic acid (EPA), docosahexaenoic acid (DHA), lovage and an extract thereof, elemi or an extract thereof, clove or an extract thereof, citronella or an extract thereof, bay or an extract thereof, cinnamon or an extract thereof, davana or an extract thereof, hemp seed or an extract thereof, poppy seed or an extract thereof, and ashitaba chalcone can be used as the PPARγ activator of the present invention. Among them, ginger or an extract thereof, nutmeg or an extract thereof, DHA, EPA, fish oil containing EPA and/or DHA, clove or an extract thereof, cinnamon or an extract thereof, and bay or an extract thereof are preferred.

The Smad3 inhibitor used in the present invention means a substance having an inhibiting action of an intracellular signaling pathway mediated by Smad3. Examples thereof include Smad3 phosphorylation inhibitors and Smad3 expression inhibitors. Other examples of the Smad3 inhibitor include a substance inhibiting the interaction between Smad3 and Smad4, TGF-β receptor antagonists, TGF-β signaling inhibitors, activin receptor antagonists, and Smad3 degradation promoters.

Typical examples of the Smad3 inhibitor include 6,7-dimethoxy-2-((2E)-3-(1-methyl-2-phenyl-1H-pyrrolo[2,3-b]pyridin-3-yl-prop-2-enoyl))-1,2,3,4-tetrahydroisoquinoline represented by the formula given below or a salt thereof (Molecular Pharmacology 69 (2) 597-607), known as a specific inhibitor of Smad3 (SIS3). A hydrochloride thereof is preferred.

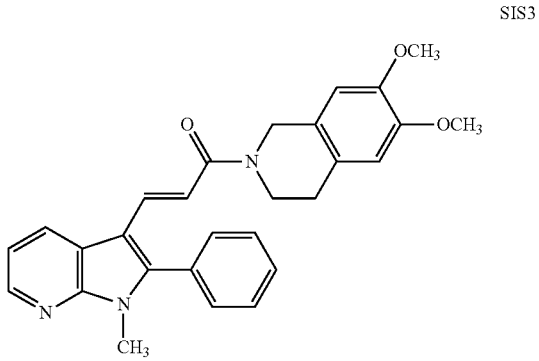 [SMILES: COc1cc2c(cc1OC)CN(C(=O)/C=C/c1c(-c3ccccc3)n(C)c3ncccc13)CC2]

SIS3

Additionally, examples of the TGF-β inhibitor effective for Smad3 inhibition may include naringenin (Pharmaceutical Research 23 (1) 82-83, 2006), SB431542 (Molecular Pharmacology 62: 58-64, 2002), LY2157299 (Proc Amer Assoc Cancer Res. 2006: 47. Abstract 250), ursolic acid (JP-A-2000-159673), oleanolic acid (JP-A-2000-159793), pyridylacrylic acid amide derivatives (International Publication No. WO 99/05109), quinazoline derivatives (JP-A-2002-523502), cyclopropanecarboxylic acid amide compounds (JP-A-2004-35475), pyridine/triazine derivatives (JP-A-2006-503043), pyrazine derivatives (JP-A-2006-519833), condensed heteroaromatic compounds (JP-A-2005-519249), isothiazole derivatives (JP-A-2006-516603), isothiazole/isoxazole derivatives (JP-A-2006-506443), pyrazole derivatives (JP-A-2006-507353), imidazole derivatives (JP-A-2006-502237), triazole derivatives (JP-A-2006-502236), triazole/oxazole derivatives (JP-A-2006-502235), quinazoline derivatives (JP-A-2007-517046), pyrimidinyl imidazole derivatives (JP-A-2008-511631 and JP-A-2008-511630), pyrazole derivatives (JP-A-2009-197016, JP-A-2009-502780, and JP-A-2004-535404), double-stranded RNA (JP-A-2011-527893), TGF-β1-inhibiting peptides (JP-A-2012-519671, JP-A-2012-214489, JP-A-2009-512727, JP-A-2008-56685, and JP-A-2007-186519), alkoxy-thienopyrimidine derivatives (JP-A-2012-530731), imidazothiadiazole derivatives (JP-A-2011-529456), thienopyrimidine derivatives (JP-A-2011-518132), triazabenzo[e]azulene derivatives (JP-A-2010-508311), triazole derivatives (JP-A-2009-520706), heterocyclic derivatives (JP-A-2006-527722), thiazole derivatives (JP-A-2006-527720), pyrazole derivatives (JP-A-2005-539026), 2-phenylpyridin-4-yl heterocyclic derivatives (JP-A-2005-539000), pyridine derivatives (JP-A-2005-537291), triazole derivatives (JP-A-2005-538997), aminothiazole derivatives (JP-A-2005-538996), benzoxazinone derivatives (JP-A-2005-530800), thiazole derivatives (JP-A-2004-521903), pyrazole derivatives (JP-A-2004-521901), thiazole derivatives (JP-A-2004-523540), thiazolamine derivatives (JP-A-2004-524302), triazole derivatives (JP-A-2004-517069), pyridinyl imidazole derivatives (JP-A-2003-524010), and triarylimidazole derivatives (JP-A-2002-541253).

As shown in Reference Examples described later, plant tannin, luteolin, a rosemary extract, a white tea extract, a milk thistle extract, a logwood dye, a peanut testa extract, litchi polyphenol, apple polyphenol, an oolong tea extract, and allspice have been confirmed to have a Smad3-inhibiting action, and plant tannin, luteolin, rosemary or an extract thereof, white tea or an extract thereof, milk thistle or an extract thereof, a logwood dye, peanut testa or an extract thereof, litchi polyphenol, apple polyphenol, oolong tea or an extract thereof, and allspice can be used as the Smad3 inhibitor of the present invention. Among them, plant tannin, rosemary or an extract thereof, allspice, and luteolin are preferred.

Examples of treatment for inhibiting Smad3 include treatments for inhibiting an intracellular signaling pathway mediated by Smad3, for example, treatments for inhibiting Smad3 phosphorylation or inhibiting Smad3 expression, and specifically include hyperthermic treatment (JP-A-2009-226069).

Examples of a suitable combination of the PPARγ activator and the Smad3 inhibitor include a combination of a thiazolidine derivative and the Smad3 inhibitor, preferably a combination of rosiglitazone (rosiglitazone maleate) or pioglitazone and SIS3, more preferably a combination of rosiglitazone (rosiglitazone maleate) and SIS3, from the viewpoint of induction of UCP-1 expression.

The β3 adrenaline receptor activator used in the present invention means a substance activating the β3 adrenaline receptor by stimulation. The activated β3 adrenaline receptor is known to promote the formation of cAMP and increase the UCP1 expression to thereby cause a lipolysis-promoting action, a heat production-promoting action, a hypoglycemic action, an antihyperlipidemic action, an intestinal motility-inhibiting action, a glucose uptake-promoting action, an antidepressant action, and the like.

Typical examples or the β3 adrenaline receptor activator include norepinephrine, epinephrine, CL316,243, mirabegron, amibegron, solabegron, L-796,568, LY-368,842, and Ro40-2148. Alternatively, an agent activating sympathetic nerve may be used. Examples thereof include capsaicin, capsiate, allicin, and paradol having a TRPV1-activating action (Pharmacology & Therapeutics 106: 179-208, 2005).

The TGR5 activator used in the present invention means a substance activating a G protein-coupled receptor TGR5 by stimulation. The activated TGR5 is known to increase intracellular cAMP and activate D2 gene to thereby promote the conversion of a thyroid hormone T4 to T3 and promote heat production, basal metabolism, and fat burning (β-oxidation).

Typical examples of the TGR5 activator include bile acid, deoxycholic acid, chenodeoxycholic acid, taurocholic acid, glycolic acid, ursodeoxycholic acid, nomilin (JP-A-2011-241189), TGR5 modulators (JP-A-2012-509348), TGR5 modulators (JP-A-2012-509349), TR5 agonists (JP-A-2013-513605, condensed ring compounds (JP-A-2004-346059), condensed ring compounds (JP-A-2006-56881), TGR5 receptor agonists (JP-A-2006-63064), and ionones (JP-A-2013-173713).

As shown in Reference Examples described later, cholic acid, a mint extract, a fermented guava tea extract, an olive tea extract, an olive leaf extract, a lemon balm extract, a hyssop extract, a glycyrrhiza extract, a hawthorn berry extract, a marjoram extract, a mate tea extract, a banaba leaf extract, a perilla extract, soybean saponin, a jujube seed extract, a basil extract, a lotus root extract, a persimmon leaf tea extract, a dill extract, a spearmint extract, a blackcurrant dye, a bacopa monniera extract, saponin, a nutmeg extract, gingerol, a loquat tea extract, a red ginger extract-P, and a chaste tree extract have been confirmed to have a TGR5-activating action, and cholic acid, mint or an extract thereof, fermented guava tea or an extract thereof, olive tea or an extract thereof, olive leaf or an extract thereof, lemon balm or an extract thereof, hyssop or an extract thereof, glycyrrhiza or an extract thereof, hawthorn berry or an extract thereof, marjoram or an extract thereof, mate tea or an extract thereof, banaba leaf or an extract thereof, a perilla extract, soybean saponin, jujube seed or an extract thereof, basil or an extract thereof, lotus root or an extract thereof, persimmon leaf tea or an extract thereof, dill or an extract thereof, spearmint or an extract thereof, a blackcurrant dye, bacopa monniera, saponin, nutmeg or an extract thereof, gingerol, loquat tea or an extract thereof, red ginger extract-P, and chaste tree or an extract thereof can be used as the TGR5 activator. Among them, bile acid, fermented guava tea, olive tea, and cholic acids are preferred.

Examples of the treatment for activating β3 adrenaline receptor or TGR5 include treatments for activating an intracellular signaling pathway mediated by β3 adrenaline receptor or TGR5, and treatments for promoting the expression of β3 adrenaline receptor or TGR5, and specifically include cold treatment (Physiol Rev 84: 277-359, 2004).

Examples of a suitable combination of the PPARγ activator, the Smad3 inhibitor, and the β3 adrenaline receptor activator or the TGR5 activator include a combination of a thiazolidine derivative, the Smad3 inhibitor, and the β3 adrenaline receptor activator or the TGR5 activator, preferably a combination of rosiglitazone (rosiglitazone maleate) or pioglitazone, SIS3 or SB431542, and CL316,243, mirabegron, or norepinephrine, more preferably a combination of rosiglitazone (rosiglitazone maleate), SIS3, and CL316,243, from the viewpoint of induction of UCP-1 expression.

The UCP-1 expression promoter, the promoter of conversion to brown adipose, the energy consumption promoter, the body fat accumulation inhibitor, the preventive or ameliorative agent for obesity, the preventive or ameliorative agent for diabetes mellitus, and the preventive or ameliorative agent for hyperlipidemia of the present invention comprising a PPARγ activator and a Smad3 inhibitor in combination, or the UCP-1 expression promoter, the promoter of conversion to brown adipose, the energy consumption promoter, the body fat accumulation inhibitor, the preventive or ameliorative agent for obesity, the preventive or ameliorative agent for diabetes mellitus, the preventive or ameliorative agent for hyperlipidemia, the lipid burning promoter, the carbohydrate metabolism-improving agent, the lipid metabolism-improving agent, or the adiponectin production promoter of the present invention comprising a PPARγ activator, a Smad3 inhibitor, and a β3 adrenaline receptor activator or a TGR5 activator in combination may be a preparation in a single dosage form containing effective amounts of these ingredients at an appropriate mixing ratio as a combination drug, or may be a kit which allows ingestion of single preparations of drugs respectively containing effective amounts of these ingredients at the same time or separately in a staggered manner. The simultaneous ingestion of these ingredients is preferred.

The treatment for inhibiting Smad3 may be performed at the same time with administration of the PPARγ activator or in a staggered manner therewith. Preferably, the treatment is performed at the same time with administration of the agent.

The treatment for inhibiting Smad3 and the treatment for activating β3 adrenaline receptor or TGR5 may be performed at the same time with the administration of the agent or in a staggered manner therewith. Preferably, the treatments are performed at the same time with the administration of the agent.

In the case of a combination drug comprising the PPARγ activator and the Smad3 inhibitor in combination, the mixing ratio thereof may be appropriately selected according to materials, use, or type of the preparation and is generally a PPARγ activator:Smad3 inhibitor ratio of 1:0.001 to 10,000, preferably 1:0.01 to 1,000, more preferably 1:0.02 to 100.

In the case of a combination drug comprising the PPARγ activator, the Smad3 inhibitor, and the β3 adrenaline receptor activator or the TGR5 activator in combination, the mixing ratio thereof may be appropriately selected according to materials, use, or type of the preparation and is generally a PPARγ activator:Smad3 inhibitor:β3 adrenaline receptor activator or TGR5 activator ratio of 1:0.001 to 10,000:0.001 to 10,000, preferably 1:0.01 to 1,000:0.01 to 1,000, more preferably 1:0.02 to 100:0.02 to 100.

As shown in Examples described later, when the PPARγ activator and the Smad3 inhibitor are added in combination to rat subcutaneous fat-derived cultured cells, the expression of the UCP-1 gene is significantly increased. Also, when the PPARγ activator and the Smad3 inhibitor are administered in combination to rats, the expression of the UCP-1 gene is significantly increased in the subcutaneous fat. These effects exceed additive effects obtained by adding or administering the PPARγ activator and the Smad3 inhibitor each alone, and are synergistic effects.

In short, a combined use of the PPARγ activator and the Smad3 inhibitor or the treatment for inhibiting Smad3 can be used for promoting UCP-1 expression or browning adipose cells, for example, as a UCP-1 expression promoter or a promoter of conversion to brown adipose, and can also be used for producing the UCP-1 expression promoter or the promoter of conversion to brown adipose.

As shown in Examples described later, when the PPARγ activator, the Smad3 inhibitor, and the β3 adrenaline receptor activator or the TGR5 activator are added in combination to rat subcutaneous fat-derived cultured cells, the expression of the UCP-1 gene is significantly increased. Also, when the PPARγ activator, the Smad3 inhibitor, and the β3 adrenaline receptor activator or the TGR5 activator are administered in combination to rats, the expression of the UCP-1 gene is significantly increased in the subcutaneous fat. These effects exceed the additive effects obtained by adding or administering the PPARγ activator, the Smad3 inhibitor, and the β3 adrenaline receptor activator or the TGR5 activator each alone, and are synergistic effects.

In short, the combined use of the PPARγ activator, the Smad3 inhibitor or the treatment for inhibiting Smad3, and the β3 adrenaline receptor activator or the TGR5 activator or the treatment for activating β3 adrenaline receptor or TGR5 can be used for promoting UCP-1 expression or browning adipose cells, for example, as a UCP-1 expression promoter or a promoter of conversion to brown adipose, and can also be used for producing the UCP-1 expression promoter or the promoter of conversion to brown adipose.

The promoted expression of UCP-1 is considered to promote heat production and consequently increase energy consumption, improve lipid metabolism and blood glucose levels, and inhibit fat accumulation or obesity (Non Patent Literature 1 described above). In fact, the PPARγ activator and the Smad3 inhibitor used in combination remarkably decreased a blood glucose level, a serum insulin level, a triglyceride (TG) level, and a NEFA (fatty acid) level, demonstrating a carbohydrate metabolism-improving action and a lipid metabolism-improving action (Example A3).

Thus, the combined use of the PPARγ activator and the Smad3 inhibitor or the treatment for inhibiting Smad3 can be used for the promotion of energy consumption, the inhibition of body fat accumulation, the prevention or amelioration of obesity, the prevention or amelioration of diabetes mellitus, and the prevention or amelioration of hyperlipidemia, for example, as an energy consumption promoter, a body fat accumulation inhibitor, a preventive or ameliorative agent for obesity, a preventive or ameliorative agent for diabetes mellitus, and a preventive or ameliorative agent for hyperlipidemia, and can also be used for producing the energy consumption promoter, the body fat accumulation inhibitor, the preventive or ameliorative agent for obesity, the preventive or ameliorative agent for diabetes mellitus, and the preventive or ameliorative agent for hyperlipidemia.

The PPARγ activator, the Smad3 inhibitor, and the β3 adrenaline receptor activator or the TGR5 activator used in combination increased the amount of lipid burned and also elevated a rectal temperature, demonstrating an energy consumption-promoting action and a lipid burning-promoting action (Example B3). Furthermore, the PPARγ activator, the Smad3 inhibitor, and the β3 adrenaline receptor activator or the TGR5 activator used in combination remarkably decreased a blood glucose level, a serum insulin level, a triglyceride (TG) level, and a NEFA (fatty acid) level, demonstrating a carbohydrate metabolism-improving action and a lipid, metabolism-improving action (Example B4).

In addition, the PPARγ activator, the Smad3 inhibitor, and the β3 adrenaline receptor activator or the TGR5 activator used in combination remarkably decreased a body weight and an adipose tissue weight, demonstrating a fat accumulation-inhibiting action and an obesity-preventing or -ameliorating action (Example B5). It is considered that the promoted expression of UCP-1 increased heat production, thereby decreasing body fat while reducing the size of white adipose cells and increasing blood adiponectin levels (Example B6).

Thus, the combined use of the PPARγ activator, the Smad3 inhibitor, and the β3 adrenaline receptor activator or the TGR5 activator can be used for the promotion of energy consumption, the inhibition of body fat accumulation, the prevention or amelioration of obesity, the prevention or amelioration of diabetes mellitus, and the prevention or amelioration of hyperlipidemia, for example, as an energy consumption promoter, a body fat accumulation inhibitor, a preventive or ameliorative agent for obesity, a preventive or ameliorative agent for diabetes mellitus, and a preventive or ameliorative agent for hyperlipidemia, and can also be used for producing the energy consumption promoter, the body fat accumulation inhibitor, the preventive or ameliorative agent for obesity, the preventive or ameliorative agent for diabetes mellitus, and the preventive or ameliorative agent for hyperlipidemia.

In this context, the use can be use in humans or nonhuman animals, or specimens derived therefrom and may be therapeutic use or nontherapeutic use.

In this context, the term "nontherapeutic" conceptually excludes medical practice, i.e., conceptually excludes methods of surgery, therapy, or diagnosis of humans, more specifically conceptually excludes methods of practicing surgery, therapy, or diagnosis on humans by medical doctors or those who are directed by medical doctors.

In this context, examples of the "promotion of UCP-1 expression" include the induction or promotion of transcribing the UCP-1 gene to UCP-1 mRNA, and the induction or promotion of translating the UCP-1 mRNA to the UCP-1 protein.

The "promotion of conversion to brown adipose" means the induction or promotion of converting white adipose to brown adipose, or the induction or promotion of the differentiating preadipocytes into brown adipose (cells). The "conversion to brown adipose" refers to changing the character of white adipose to that characteristic to brown adipose, or the inducing adipose cells having a character of brown adipose (cells) from preadipocytes, Specifically, histological examples thereof include reduction in cell size specific for brown adipose cells, exhibition of multilocular neutral fat accumulation structure or the like, increase in mitochondria, and expression of UCP-1 known as a marker molecule for brown adipose cells at the mRNA or protein level.

In the present invention, it should be understood that the "brown adipose (cells)" includes adipose (cells) called "Beige adipose (cells)" or "Brite adipose (cells)" as well as "classic brown adipose (cells)", and the "conversion to brown adipose" includes "conversion to classic brown adipose", "conversion to Beige adipose", and "conversion to Brite adipose" (Kosaku Shinoda, Shingo Kajimura: Cell Technology, Vol. 32, No. 7, 769-773, 2013).

The "promotion of lipid burning" means the promotion of burning (oxidizing) lipids, particularly, fatty acids, derived from diet or derived from fat accumulated in the body.

The "promotion of adiponectin production" means increase in the expression of adiponectin mRNA and/or protein in adiponectin-producing tissues, and increase in the amount of adiponectin mRNA and/or protein produced by inhibiting the degradation of the adiponectin mRNA and/or protein, and also conceptually includes the resulting increase in the amount of adiponectin secreted and rise in serum adiponectin concentration.

Thus, the UCP-1 expression promoter, the promoter of conversion to brown adipose, the energy consumption promoter, the body fat accumulation inhibitor, the preventive or ameliorative agent for obesity, the preventive or ameliorative agent for diabetes mellitus, the preventive or ameliorative agent for hyperlipidemia, the lipid burning promoter, the carbohydrate metabolism-improving agent, the lipid metabolism-improving agent, and the adiponectin production promoter (hereinafter, collectively referred to as a "UCP-1 expression promoter, etc.") of the present invention is useful as a drug, a quasi-drug, or a dermatological preparation for external use which exerts each effect of promoting UCP-1 expression, browning adipose cells, promoting energy consumption, inhibiting body fat accumulation, preventing or ameliorating obesity, preventing or ameliorating diabetes mellitus, preventing or ameliorating hyperlipidemia, promoting lipid burning, improving carbohydrate metabolism, improving lipid metabolism, and promoting adiponectin production-promoting effect, or as a material or a preparation to be contained in such a drug, a quasi-drug, or a dermatological preparation for external use, or a food product.

The dosage form of the drug described above (also including the quasi-drug) may be any of, for example, an injection, a suppository, an inhalant, a transdermal absorption preparation, various preparations for external use, a tablet, a capsule, granules, a powder, and a syrup, and its administration mode may be any of oral administration (internal use) and parenteral administration (external use and injection). In order to prepare such pharmaceutical preparations in various dosage forms, for example, the PPARγ activator and the Smad3 inhibitor of the present invention, or the PPARγ activator, the Smad3 inhibitor, and the β3 adrenaline receptor activator or the TGR5 activator of the present invention may be used in appropriate combination with an additional pharmaceutically acceptable excipient, binder, expander, disintegrant, surfactant, lubricant, dispersant, buffer, preservative, corrigent, fragrance, coating agent, carrier, diluent, other medicinal ingredients, etc.

The dermatological preparation for external use described above (also including the quasi-drug) may be provided in various dosage forms such as lotions, emulsions, gels, creams, ointments, powders, and granules according to a use method. Such dermatological preparations for external use in various dosage forms may be prepared by appropriately combining, for example, the PPARγ activator, and the Smad3 inhibitor, and additionally the β3 adrenaline receptor activator or the TGR5 activator of the present invention with an oil ingredient, a humectant, a powder, a dye, an emulsifier, a solubilizer, a detergent, an ultraviolet absorber, a thickener, a medicinal ingredient, a fragrance, a resin, a bactericidal or fungicidal agent, a plant extract, alcohols, etc., which may be contained in the dermatological preparation for external use.

Examples of the medicinal ingredient which may be added to the drug or the dermatological preparation for external use (also including the quasi-drug) include vitamins, and chemicals or natural products known to have a fat metabolism-promoting effect (e.g., xanthine derivatives, α-adrenergic blockers, PPARα activators, PPARδ activators, bipyridine derivatives, isoflavone acid, grapefruit oil, nootkatone, caffeine, chili pepper or an extract thereof, capsaicin, or analogs thereof, resveratrol, cocoa polyphenol, coffee polyphenol, chlorogenic acid, ferulic acid, quercetin, hesperidin and glycosides thereof, astaxanthin, α-lipoic acid, and phospholipid).

The content of the PPARγ activator in the drug or the dermatological preparation for external use (also including the quasi-drug) is usually 0.01 mass % or larger, preferably 0.1 mass % or larger, more preferably 1.0 mass % or larger, and 95 mass % or smaller, preferably 80 mass % or smaller, more preferably 60 mass % or smaller, of the total mass of the preparation. Also, the content is, for example, from 0.01 to 95 mass %, preferably from 0.1 to 80 mass %, more preferably from 1.0 mass % to 60 mass %.

The content of the Smad3 inhibitor is 0.01 mass % or larger, preferably 0.1 mass % or larger, more preferably 1.0 mass % or larger, and 95 mass % or smaller, preferably 80 mass % or smaller, more preferably 60 mass % or smaller, of the total mass of the preparation. Also, the content is, for example, from 0.01 to 95 mass %, preferably from 0.1 to 80 mass %, more preferably from 1.0 mass % to 60 mass %.

The content of the β3 adrenaline receptor activator or the TGR5 activator is 0.01 mass % or larger, preferably 0.1 mass % or larger, more preferably 1.0 mass % or larger, and 85 mass % or smaller, preferably 80 mass % or smaller, more preferably 60 mass % or smaller, of the total mass of the preparation. Also, the content is, for example, from 0.01 to 95 mass %, preferably from 0.1 to 80 mass %, more preferably from 1.0 mass % to 60 mass %.

The food product described above encompasses foods for patients, and functional foods such as foods with nutrient function and foods for specified health use which are conceptually based on the promotion of energy consumption, the inhibition of body fat accumulation, the prevention or amelioration of obesity, the prevention or amelioration of diabetes mellitus, the prevention or amelioration of hyperlipidemia, the promotion of lipid burning, the improvement of carbohydrate metabolism, the improvement of lipid metabolism, etc., and, if necessary, indicate this concept.

The form of the food product may be a solid, semisolid, or liquid form. Examples of the food product include breads, noodles, confectionery such as cookies, jellies, dairy products, frozen meals, ready-to-eat meals, processed starch, products, processed meat products, other processed food products, drinks such as tea or coffee drinks, fruit juice drinks, carbonate drinks, and jelly-like drinks, soups, seasonings, nutritional supplements, and raw materials thereof. The food product may be in a supplement-like form such as a tablet, pill, capsule, solution, syrup, powder, or granule form, as with the oral administration preparations described above.

These food products may be prepared by appropriately combining and mixing arbitrary food or drink, materials, a solvent, a softening agent, an oil, an emulsifier, an antiseptic, a flavor, a stabilize, a colorant, an antioxidant, a thickener, a fixing agent, a dispersant, a wetting agent, etc. Also, the food product may be appropriately supplemented with a medicinal ingredient including vitamins, and chemicals or natural products known to have a fat metabolism-promoting effect (e.g., isoflavone acid, grapefruit, oil, nootkatone, caffeine, chili pepper or an extract thereof, capsaicin or analogs thereof, resveratrol, cocoa polyphenol, coffee polyphenol, chlorogenic acid, ferulic acid, quercetin, hesperidin and glycosides thereof, astaxanthin, α-lipoic acid, and phospholipid).

The content of the PPARγ activator in the food product differs depending on a use form thereof and is usually 0.0001 mass % or larger, preferably 0.001 mass % or larger, more preferably 0.0.1 mass % or larger, and 50 mass % or smaller, preferably 20 mass % or smaller, more preferably 10 mass % or smaller. The content is, for example, from 0.0001% to 50 mass %, preferably from 0.001 to 20 mass %, more preferably from 0.01 to 10 mass %.

The content of the Smad3 inhibitor in the food product is 0.0001 mass % or larger, preferably 0.001 mass % or larger, more preferably 0.01 mass % or larger, and 50 mass % or smaller, preferably 20 mass % or smaller, more preferably 10 mass % or smaller. The content is, for example, from 0.0001% to 50 mass %, preferably from 0.001 to 20 mass %, more preferably from 0.01 to 10 mass %.

The content of the β3 adrenaline receptor activator or the TGR5 activator in the food product is 0.0001 mass % or larger, preferably 0.001 mass % or larger, more preferably 0.01 mass % or larger, and 50 mass % or smaller, preferably 20 mass % or smaller, more preferably 10 mass % or smaller. The content is, for example, from 0.0001% to 50 mass %, preferably from 0.001 to 20 mass %, more preferably from 0.01 to 10 mass %.

In the case of using the combination of the PPARγ activator and the Smad3 inhibitor of the present invention as a drug or a supplement or as components for a drug or a supplement, their doses may vary according to the types of the PPARγ activator and the Smad3 inhibitor and the condition, body weight, sex, age, or other factors of a subject. The daily doses thereof per adult for oral administration involve usually 1 mg or larger, preferably 5 mg or larger, more preferably 15 mg or larger, and 10 g or smaller, preferably 5 g or smaller, more preferably 1 g or smaller, of the PPARγ activator. For pioglitazone, the daily dose is usually from 5 mg to 45 mg, particularly preferably from 15 mg to 45 mg. For rosiglitazone, the daily dose is usually from 1 mg to 8 mg, particularly preferably from 4 mg to 8 mg. The daily doses thereof per adult for oral administration also involve 1 mg or larger, preferably 5 mg or larger, more preferably 15 mg or larger, and 10 g or smaller, preferably 5 g or smaller, more preferably 1 g or smaller, of the Smad3 inhibitor.

In the case of using the combination of the PPARγ activator, the Smad3 inhibitor, and the β3 adrenaline receptor activator or the TGR5 activator of the present invention as a drug or a supplement or as components for a drug or a supplement, their doses may vary according to the types of the PPARγ activator, the Smad3 inhibitor, and the β3 adrenaline receptor activator or the TGR5 activator and the condition, body weight, sex, age, or other factors of a subject.

The daily doses thereof per adult for oral administration involve usually 1 mg or larger, preferably 5 mg or larger, more preferably 15 mg or larger, and 10 g or smaller, preferably 5 g or smaller, more preferably 1 g or smaller, of the PPARγ activator. For pioglitazone, the daily dose is usually from 1 mg to 45 mg, particularly preferably from 15 mg to 45 mg. For rosiglitazone, the daily dose is usually from 1 mg to 8 mg, particularly preferably from 4 mg to 8 mg. The daily doses thereof per adult for oral administration also involve 1 mg or larger, preferably 5 mg or larger, more preferably 15 mg or larger, and 10 g or smaller, preferably 5 g or smaller, more preferably 1 g or smaller, of the Smad3 inhibitor; and 1 mg or larger, preferably 5 mg or larger, more preferably 15 mg or larger, and 10 g or smaller, preferably 5 g or smaller, more preferably 1 g or smaller, of the β3 adrenaline receptor activator or the TGR5 activator. For mirabegron, the daily dose, is usually from 5 to 100 mg, particularly preferably from 25 to 50 mg.

These, preparations can be administered according to arbitrary dosing schedules and, preferably, are continuously administered once a day or in several divided portions per day for several weeks to several months.

The subject for the administration or the ingestion is not particularly limited as long as the subject is an animal which needs or desires it. Examples thereof include humans who need or desire the promotion of energy consumption, the inhibit ism of body fat accumulation, the prevention or amelioration of obesity, the promotion of lipid burning, the improvement of carbohydrate metabolism, or the improvement of lipid metabolism.

As for the embodiments mentioned above, the present invention further discloses the following aspects:

<1> A UCP-1 expression promoter comprising a PPARγ activator and a Smad3 inhibitor in combination.

<2> A promoter of conversion to brown adipose comprising a PPARγ activator and a Smad3 inhibitor in combination.

<3> An energy consumption promoter comprising a PPARγ activator and a Smad3 inhibitor in combination.

<4> A body fat accumulation inhibitor comprising a PPARγ activator and a Smad3 inhibitor in combination.

<5> A preventive or ameliorative agent for obesity comprising a PPARγ activator and a Smad3 inhibitor in combination.

<6> A preventive or ameliorative agent for diabetes mellitus comprising a PPARγ activator and a Smad3 inhibitor in combination.

<7> A preventive or ameliorative agent for hyperlipidemia comprising a PPARγ activator and a Smad3 inhibitor in combination.

<8> Use of a PPARγ activator and a Smad3 inhibitor in combination for producing a UCP-1 expression promoter, a promoter of conversion to brown adipose, an energy consumption promoter, a body fat accumulation inhibitor, a preventive or ameliorative agent for obesity, a preventive or ameliorative agent for diabetes mellitus, or a preventive or ameliorative agent for hyperlipidemia.

<9> A combination of a PPARγ activator and a Smad3 inhibitor for use in promotion of UCP-1 expression, promotion of conversion to brown adipose, promotion of energy consumption, inhibition of body fat accumulation, prevention or amelioration of obesity, prevention or amelioration of diabetes mellitus, or prevention or amelioration of hyperlipidemia.

<10> A method for promoting UCP-1 expression, a method for promoting conversion to brown adipose, a method for promoting energy consumption, a method for inhibiting body fat accumulation, a method for preventing or ameliorating obesity, a method for preventing or ameliorating diabetes mellitus, or a method for preventing or ameliorating hyperlipidemia, comprising administering or ingesting effective amounts of a PPARγ activator and a Smad3 inhibitor in combination, or combining the ingestion or administration of a PPARγ activator with a treatment for inhibiting Smad3.

<11> In above <1> to <10>, the PPARγ activator is rosiglitazone or pioglitazone.

<12> In above <1> to <10>, the PPARγ activator is any one or more selected from the group consisting of ginger or an extract thereof, nutmeg or an extract thereof, eicosapentaenoic acid (EPA), docosahexaenoic acid (DHA), elemi or an extract thereof, clove or an extract thereof, citronella or an extract thereof, bay or an extract thereof, cinnamon or an extract thereof, ashitaba chalcone, lovage or an extract thereof, davana or an extract thereof, poppy seed or an extract thereof, and hemp seed or an extract thereof.

<13> In above <1> to <12>, the Smad3 inhibitor is SIS3.

<14> In above <1> to <12>, the Smad3 inhibitor is any one or more selected from the group consisting of plant tannin, luteolin, rosemary or an extract thereof, white tea or an extract thereof, milk thistle or an extract thereof, logwood dye, peanut testa or an extract thereof, litchi polyphenol, apple polyphenol, oolong tea, and allspice.

<15> In above <8>, the use is nontherapeutic use.

<16> In above <10>, the method is a nontherapeutic method.

<17> In above <10>, a subject for the administration or the ingestion is a human who needs or desires the promotion of energy consumption, the inhibition of body fat accumulation, the prevention or amelioration of obesity, the prevention or amelioration of diabetes mellitus, or the prevention or amelioration of hyperlipidemia.

<18> In above <1> to <17>, the daily doses per adult in oral administration of the PPARγ activator and the Smad3 inhibitor as a drug or a supplement are 1 mg or larger, preferably 5 mg or larger, more preferably 15 mg or larger, and 10 g or smaller, preferably 5 g or smaller, more preferably 1 g or smaller, of the PPARγ activator, and 1 mg or larger, preferably 5 mg or larger, more preferably 15 mg or larger, and 10 g or smaller, preferably 5 g or smaller, more preferably 1 g or smaller, of the Smad-3 inhibitor.

<19> A UCP-1 expression promoter comprising a PPARγ activator, a Smad3 inhibitor, and a β3 adrenaline receptor activator or a TGR5 activator in combination.

<20> A promoter of conversion to brown adipose comprising a PPARγ activator, a Smad3 inhibitor, and a β3 adrenaline receptor activator or a TGR5 activator in combination.

<21> An energy consumption promoter comprising a PPARγ activator, a Smad3 inhibitor, and a β3 adrenaline receptor activator or a TGR5 activator in combination.

<22> A body fat accumulation inhibitor comprising a PPARγ activator, a Smad3 inhibitor, and a β3 adrenaline receptor activator or a TGR5 activator in combination.

<23> A preventive or ameliorative agent for obesity comprising a PPARγ activator, a Smad3 inhibitor, and a β3 adrenaline receptor activator or a TGR5 activator in combination.

<24> A preventive or ameliorative agent for diabetes mellitus comprising a PPARγ activator, a Smad3 inhibitor, and a β3 adrenaline receptor activator or a TGR5 activator in combination.

<25> A preventive or ameliorative agent for hyperlipidemia comprising a PPARγ activator, a Smad3 inhibitor, and a β3 adrenaline receptor activator or a TGR5 activator in combination.

<26> A lipid burning promoter comprising a PPARγ activator, a Smad3 inhibitor, and a β3 adrenaline receptor activator or a TGR5 activator in combination.

<27> A carbohydrate metabolism-improving agent comprising a PPARγ activator, a Smad3 inhibitor, and a β3 adrenaline receptor activator or a TGR5 activator in combination.

<28> A lipid, metabolism-improving agent comprising a PPARγ activator, a Smad3 inhibitor, and a β3 adrenaline receptor activator or a TGR5 activator in combination.

<29> An adiponectin production promoter comprising a PPARγ activator, a Smad3 inhibitor, and a β3 adrenaline receptor activator or a TGR5 activator in combination.

<30> Use of a PPARγ activator, a Smad3 inhibitor, and a β3 adrenaline receptor activator or a TGR5 activator in combination for producing a UCP-1 expression promoter, a promoter of conversion to brown adipose, an energy consumption promoter, a body fat accumulation inhibitor, a preventive or ameliorative agent for obesity, a preventive or ameliorative agent for diabetes mellitus, a preventive or ameliorative agent for hyperlipidemia, a lipid burning promoter, a carbohydrate, metabolism-improving agent, a lipid metabolism-improving agent, or an adiponectin production promoter.

<31> A combination of a PPARγ activator, a Smad3 inhibitor, and a β3 adrenaline receptor activator or a TGR5 activator for use in promotion of UCP-1 expression, promotion of conversion to brown adipose, promotion of energy consumption, inhibition of body fat accumulation, prevention or amelioration of obesity, prevention or amelioration of diabetes mellitus, prevention or amelioration of hyperlipidemia, promotion of lipid burning, improvement of carbohydrate metabolism, improvement of lipid metabolism, or promotion of adiponectin production.

<32> A method for promoting UCP-1 expression, a method for promoting conversion to brown adipose, a method for promoting energy consumption, a method for inhibiting body fat accumulation, a method for preventing or ameliorating obesity, a method for preventing or ameliorating diabetes mellitus, a method for preventing or ameliorating hyperlipidemia, a method for promoting lipid burning, a method for improving carbohydrate metabolism, a method for improving lipid metabolism, or a method for promoting adiponectin production, comprising combining ingestion or administration of a PPARγ activator, ingestion or administration of a Smad3 inhibitor or a treatment for inhibiting Smad3, and ingestion or administration of a β3 adrenaline receptor activator or a TGR5 activator or a treatment for activating β3 adrenaline receptor or TGR5.

<33> In above <19> to <32>, the PPARγ activator is rosiglitazone or pioglitazone.

<34> In above <19> to <32>, the PPARγ activator is any one or more selected from the group consisting of ginger or an extract thereof, nutmeg or an extract thereof, eicosapentaenoic acid (EPA), docosahexaenoic acid (DHA), elemi or an extract thereof, clove or an extract thereof, citronella or an extract thereof, bay or an extract thereof, cinnamon or an extract thereof, ashitaba chalcone, lovage or an extract thereof, davana or an extract thereof, poppy seed or an extract thereof, and hemp seed or an extract thereof.

<35> In above <19> to <34>, the Smad3 inhibitor is SIS3 or SB431542.

<36> In above <19> to <34>, the Smad3 inhibitor is any one or more selected from the group consisting of plant tannin, luteolin, rosemary or an extract thereof, white tea or an extract thereof, milk thistle or an extract thereof, logwood dye, peanut testa or an extract thereof, litchi polyphenol, apple polyphenol, oolong tea, and allspice.

<37> in above <19> to <36>, the β3 adrenaline receptor activator is norepinephrine, CL316,243, or mirabegron.

<38> In above <19> to <36>, the TGR5 activator is any one or more selected from the group consisting of cholic acid, mint or an extract thereof, fermented guava tea or an extract thereof, olive tea or an extract thereof, olive leaf or an extract thereof, lemon balm or an extract thereof, hyssop or an extract thereof, glycyrrhiza or an extract thereof, hawthorn berry or an extract thereof, marjoram or an extract thereof, mate tea or an extract thereof, banaba leaf or an extract thereof, a perilla extract, soybean saponin, jujube seed or an extract thereof, basil or an extract thereof, lotus root or an extract thereof, persimmon leaf tea or an extract thereof, dill or an extract thereof, spearmint or an extract thereof, blackcurrant dye, bacopa monniera, saponin, nutmeg or an extract thereof, gingerol, loquat tea or an extract thereof, red ginger extract-P, and chaste tree or an extract thereof.

<39> In above <30>, the use is nontherapeutic use.

<40> In above <32>, the method is a nontherapeutic method.

<41> In above <32>, a subject for the administration or the ingestion is a human who needs or desires the promotion of energy consumption, the inhibition of body fat accumulation, the prevention or amelioration of obesity, the prevention or amelioration of diabetes mellitus, the prevention or amelioration of hyperlipidemia, or the promotion of adiponectin production.

EXAMPLES

Example A1 UCP-1 Expression-Inducing Action
(Cell)

(1) Isolation and Culture of Adipose Cells

Wistar rats (SLC, male, 8 weeks old) were used. For diet, each rat was allowed to freely eat standard solid feed CE-2 (Oriental Yeast Co., Ltd.) and freely drink tap water. The breeding environment was set to room temperature of 23±2° C., a humidity of 55±10%, and a light period of 7 a.m. to 7 p.m.

The rat was subjected to abdominal section under isoflurane anesthesia, and abdominal subcutaneous fat was excised. The adipose tissues were chopped with a knife, then suspended in a 0.5 mg/mL collagenase solution, and incubated at 37° C. for 15 minutes to separate and disperse cells. Immediately after addition of an appropriate medium, the cells were centrifuged at 1,000 rpm for 5 minutes, and the supernatant was removed. A stromal vascular fraction (SVF) obtained as precipitates was suspended in a medium, and this suspension was used as adipose tissue-derived cultured precursor cells.

The medium used was high glucose DMEM (Sigma-Aldrich Corp.) supplemented with 10% fetal bovine serum (FBS, AusGeneX PTY LTD.), 100 units/mL penicillin (Invitrogen Corp.), and 100 μg/mL streptomycin (Invitrogen Corp.) in which the culture was performed at 37° C. under 5% $CO_2$ conditions.

(2) Induction of UCP-1 Expression

The obtained cultured precursor cells were inoculated to a 12-well plate coated with type I collagen. On the next day, the PPARγ activator (rosiglitazone (Rosi) (Wako Pure Chemical Industries, Ltd.), 1 μM) and/or the Smad3 inhibitor (SIS3 (Sigma-Aldrich Corp.), 10 μM) was added thereto.

(3) Quantitative PCR

Total RNA was extracted according to a standard method using RNeasy Mini Kit (Qiagen N.V.). The total RNA was reverse-transcribed according to a standard method using High Capacity RNA-to-cDNA Kit (Applied Biosystems by Life Technologies).

Quantitative PCR was performed with the obtained cDNA (30 ng/well) as a template using 7500 Fast Real-Time PCR System (Applied Biosystems by Life Technologies). The expression level of UCP-1 gene was corrected with a 36B4 gene expression level as an internal standard.

As shown from FIG. 1, the expression level of UCP-1 was synergistically increased by the combination of rosiglitazone and SIS3.

Example A2 UCP-1 Expression-Inducing Action (Mouse)

(1) Animal and Breeding Thereof

C57BL/6J mice (SLC, male, 10 weeks old) were divided into 2 groups such that the body weight was equivalent between the groups. For diet, each mouse was allowed to freely eat standard solid feed CE-2 (Oriental Yeast Co., Ltd.) and freely drink tap water. The breeding environment was set to room temperature of 23±2° C., a humidity of 55±10%, and a light period of 7 a.m. to 7 p.m.

(2) Operation to Implant Alzet Osmotic Pump

A 1/13 diluted solution of Somnopentyl was intraperitoneally administered at 10 mL/kg body weight, and than, an analgesic pentazocine was subcutaneously injected at 1 mg/kg body weight. After shaving of the back, an osmotic pump Alzet (DURECT Corp.) filled with test compounds given below was implanted subcutaneously to thereby continuously administer the test compounds. Each test compound used was dissolved in 50% DMSO/20% ethanol/30% aqueous solution.

<Test Compound>

Group 1: control group

Group 2: PPARγ activator (rosiglitazone (Rosi) (Wako Pure Chemical Industries, Ltd.), 5 mg/kg body weight/day)+ Smad3 inhibitor (SIS3 (Sigma-Aldrich Corp.), 5 mg/kg body weight/day)

One week after the operation, inguinal subcutaneous fat was collected for analysis of a UCP-1 expression level. The collected tissues were immediately frozen using liquid nitrogen and stored at −80° C. until use. The tissues were also fixed in a 10% formalin solution for staining.

(3) Quantitative PCR

Total RNA was extracted according to a standard method using RNeasy Lipid Tissue Mini Kit (Qiagen N.V.). The total RNA was reverse-transcribed according to a standard method using High Capacity RNA-to-cDNA Kit (Applied Biosystems by Life Technologies).

Quantitative PCR was performed with the cDNA (30 ng/well) obtained by the reverse transcription as a template using 7500 Fast Real-Time PCR System (Applied Biosystems by Life Technologies). The expression level of UCP-1 gene was corrected with a 36B4 gene expression level as an internal standard.

As shown from FIG. 2 (left diagram), the expression level of UCP-1 was remarkably elevated by the combination of rosiglitazone and SIS3.

(4) Western Blotting

The tissues were added with Lysis buffer and homogenized. After removal of solidified fat layers by centrifugation at 3,000 rpm at 4° C. for 5 minutes, a supernatant centrifuged at 12,000 rpm at for 10 minutes was obtained as a protein solution.

A prepared sample containing 10 μg of the protein and a ¼ volume of 4×SDS Sample buffer (Novagen) per lane was thermally denatured at 95° C. for 5 minutes and then used in SDS-PAGE. The protein was transferred to Immun-Blot™ PVDF Membrane (Bio-Rad Laboratories, Inc.), subjected to blocking and antibody reaction by the procedures given below, and exposed using ECL prime western blotting detection system (Amersham plc), followed by detection of a band.

5% skimmed milk/TBS-T, 1 hour (room temperature)
↓ Washing with TBS-T
Primary antibody/Can Get Signal™ solution 1 (Toyobo Co., Ltd.), O/N (4° C.)
↓ Washing with TBS-T
Secondary antibody/Can Get Signal™ solution 2 (Toyobo Co., Ltd.), 1 hour (room temperature)
↓ Washing with TBS-T
Detection TBS-T: 0.1% Tween 20/tris-buffered saline (TBS)

Lysis buffer: RIPA buffer (Sigma-Aldrich Corp.), Protease inhibitor cocktail (1/1,000 amount, Sigma-Aldrich Corp.)

Primary antibody: anti-UCP-1 (Abcam #23841), diluted 1,000-fold anti-α-tubulin (Cell signaling #2144), diluted 1,000-fold Secondary antibody-, anti-rabbit IgG, HRP linked (GE Healthcare Japan Corp.), diluted 1,000-fold As shown from FIG. 3 (right diagram), the expression level of UCP-1 was remarkably increased by the combination of rosiglitazone and SIS3.

(5) Immunohistochemical Staining of UCP-1

The inguinal subcutaneous fat was subjected to immunohistochemical staining of UCP-1 according to the protocol given below. A 10% formalin solution was used in tissue fixation. The antibody used was anti-UCP-1 (Abcam #23841).

<Protocol>

1) A paraffin section is deparaffinized with xylene, washed with alcohol and water, and dipped in PBS.
2) MW treatment is performed with Dako Target Retrieval solution, pH 9 (10×) for 5 minutes.
3) After washing with PBS, treatment with 1% hydrogen peroxide in methanol is performed at room temperature for 30 minutes.
4) The resulting sample is reacted with a primary antibody diluted 300-fold at room temperature for 60 minutes.
5) After washing with PBS, the sample is reacted with Anti-Rabbit Envision at room temperature for 30 minutes.
6) After washing with PBS, color is developed with DAB, followed by nuclear staining with hematoxylin, dehydration, clearing, and embedding.

Washing with PBS: 5 minutes×3 times

<Reagent>

Primary antibody: ab23841 (Abcam plc)

Secondary antibody; Envision™ K4003 (Dako by Agilent Technologies)

DAB; K3468 (Dako by Agilent Technologies)

Dako Target Retrieval solution, pH 9: S2367 (Dako by Agilent Technologies)

The cells were reduced in size and stained dark by the combination of rosiglitazone and SIS3, as compared with the control, demonstrating that the expression of UCP-1 was induced (FIG. 3).

Example A3 Carbohydrate Metabolism- and Lipid Metabolism-Improving Actions (1) Animal and Breeding Thereof Each C57BL/6J (SLC, male, 7 weeks old) was allowed to freely eat High-Fat Diets with 60 cal % Fat (Research Diets, Inc.) and freely drink tap water. After 10 weeks, the mice were divided into 4 groups such that the average body weight was equivalent among the groups. The breeding environment was set to room temperature of 23±2° C., a humidity of 55±10%, and a light period of 7 a.m. to 7 p.m.

(2) Operation to Implant Alzet Osmotic Pump

A 1/13 diluted solution of Somnopentyl was intraperitoneally administered at 10 mL/kg body weight, and then, an analgesic pentazocine was subcutaneously injected, at 1 mg/kg body weight. After shaving of the back, an osmotic pump Alzet (DURECT Corp.) filled with the agents given below was implanted subcutaneously to thereby continuously administer the agents. Each test compound used was dissolved in 50% DMSO/20% ethanol/30% aqueous solution.

<Test Compounds>

Group 1: control group

Group 2: PPARγ activator (rosiglitazone (Rosi) (Wako Pure Chemical Industries, Ltd.), 5 mg/kg body weight/day)+Smad3 inhibitor (SIS3 (Sigma-Aldrich Corp.), 5 mg/kg body weight/day)

(3) Oral Carbohydrate and Lipid Tolerance Tests 13 days after the operation, oral carbohydrate and lipid tolerance tests were conducted by the method given below.

The following solution containing 10% glucose and 10% corn oil was emulsified by ultrasonication and then used as a carbohydrate-lipid mixed emulsion.

<Composition of Carbohydrate-Lipid Mixed Emulsions>

| | |
|---|---|
| Glucose | 1 g |
| Corn oil | 1 g |
| Egg yolk lecithin | 0.1 g |
| Fatty acid-free BSA | 0.4 g |
| Distilled water | total 10 mL |

<Method>

After fasting for 12 hours, each mouse was restrained under isoflurane anesthesia, and the carbohydrate-lipid mixed emulsion was orally administered in an amount of 10 mL/kg body weight using a probe. After 0, 15, 30, 60, and 120 minutes, blood was collected from the orbit under isoflurane anesthesia while the blood glucose level was measured. The blood glucose level was measured using a simple blood glucose level meter Accu-Chek Aviva (F. Hoffmann-La Roche, Ltd.) and a measurement test paper Accu-Chek Aviva Strip II (F. Hoffmann-La Roche, Ltd.). Serum was separated from the collected blood by centrifugation at 10,000 rpm at 4° C. for 6 minutes. The serum insulin concentration was measured using an insulin measurement kit (Morinaga Institute of Biological Science, Inc.). The serum triglyceride concentration was measured using TG E-Test (Wako Pure Chemical Industries, Ltd.). The serum free fatty acid concentration was measured using NEFA C-Test (Wako Pure Chemical Industries, Ltd.).

AUC was calculated as an area under the curve with the lowest measurement value as a base. The results are shown in FIG. 4.

As shown from FIG. 4, the blood glucose level, the serum insulin level, the triglyceride (TG) level, and the NEFA (fatty acid) level were remarkably decreased by the combination of rosiglitazone and SIS3, demonstrating a carbohydrate metabolism-improving effect and a lipid metabolism-improving effect.

Example B1 UCP-1 Expression-Inducing Action of PPARγ Activator, Smad3 Inhibitor, and β3 Adrenaline Receptor Activator (Cell)

(1) Preparation of Preadipocyte from Adipose Tissue

The abdominal subcutaneous fat tissues of a Wistar-rat (male, 8 weeks old) were chopped with a surgical knife in a collagenase buffer (0.05% collagenase+4% BSA in Hank's buffer), and then, the chopped tissues were incubated at 37° C. for 15 minutes while shaken. After addition of an appropriate amount of a medium (high glucose DMEM (Invitrogen Corp.)+10% fetal, bovine serum (FBS) (AusGeneX PTY LTD.)+100 units/mL penicillin+100 mg/mL streptomycin (Invitrogen Corp.)), the obtained cell suspension was centrifuged at 1,000 rpm for 5 minutes. The supernatant was removed to obtain pellets (SVF: stromal vascular fraction). The SVF was suspended in a DMEM (+10% FBS+penicillin+streptomycin) medium, inoculated to a T-175 flask, cultured for 4 days, and used as preadipocytes.

(2) Induction of UCP-1 Expression

The preadipocytes were inoculated to a 12-well plate coated with type I collagen. On the next day, the PPARγ activator (rosiglitazone (Rosi) (Wako Pure Chemical Industries, Ltd.), final concentration: 1 μM) and/or the Smad3 inhibitor (SIS3 (Sigma-Aldrich Corp.), final concentration: 10 μM) was added thereto. After culture for 7 days, the β3 adrenaline receptor activator (norepinephrine (NE) (Wako Pure Chemical Industries, Ltd.), final concentration: 1 μM)) was added thereto, and the cells were cultured for 2 hours, then washed with PBS, and recovered.

(3) Quantitative PCR

Total RNA was extracted according to a standard method using RNeasy Mini Kit (Qiagen N.V.). The total RNA was reverse-transcribed according to a standard method using High Capacity RNA-to-cDNA Kit (Applied Biosystems by Life Technologies).

Quantitative PCR was performed with the obtained cDNA (30 ng/well) as a template using 7500 Fast Real-Time PCR System (Applied Biosystems by Life Technologies). The expression level of each gene was corrected with a 36B4 gene expression level as an internal standard. The results obtained in the presence or absence of norepinephrine (NE) are shown in FIG. 5. Control excluded the agents described above.

As shown from FIG. 5, the expression level of UCP-1 was synergistically increased by the combination of rosiglitazone, SIS3, and norepinephrine.

(4) Contribution of PPARγ Activator

The preadipocytes (n=3) obtained as described above were inoculated to a 12-well plate coated with type I collagen. On the next day, the PPARγ activator (rosiglitazone (Rosi) (Wako Pure Chemical Industries, Ltd.) or pioglitazone (Wako Pure Chemical Industries, Ltd.); 1 μM) and the Smad3 inhibitor (SIS3 (Sigma-Aldrich Corp.), 10 μM) were added thereto. After culture for 7 days, the cells were treated with the β3 adrenaline receptor activator (norepinephrine (Wako Pure Chemical Industries, Ltd.), 1 μM) for 2 hours and then recovered.

The expression level of each gene obtained in the presence or absence of rosiglitazone or pioglitazone is shown in FIG. 6.

As shown from FIG. 6, the expression level of UCP-1 was synergistically increased by the addition of rosiglitazone or pioglitazone to SIS3 and norepinephrine.

(5) Contribution of Smad3 Inhibitor

The preadipocytes were collected by trypsin treatment and transfected with siRNA against each Smad by electroporation using Neon transfection System. (Invitrogen Corp.). The preadipocytes ($3 \times 10^5$ cells) were transfected with 50 pmol of the siRNA (Life Technologies) under conditions of 1150 V/20 ms/3 pulses, suspended in a DMEM (+10% FBS+100 units/mL penicillin+100 mg/ml streptomycin) medium, and then inoculated to a 12-well plate coated with type I collagen. After 6 hours, rosiglitazone was added thereto, and the cells were cultured with the medium replaced with fresh one every day. Four days after the inoculation, the cells were treated with norepinephrine for 2 hours and then recovered, and the UCP-1 expression level was analyzed by using RT-PCR. For a control, rosiglitazone, SIS3, and norepinephrine were added in the same approach as above to cells transfected with random siRNA, followed by analysis.

The influence of the siRNA against each Smad on the expression of the UCP-1 gene is shown in FIG. 7.

As shown from FIG. 7, the expression level of UCP-1 was remarkably increased by the knockdown of Smad3 and Smad4 with siRNA in the presence of rosiglitazone and norepinephrine.

The preadipocytes (n=3) obtained as described above were inoculated to a 12-well plate coated with type I collagen. On the next day, the PPARγ activator (rosiglitazone (Rosi) (Wako Pure Chemical Industries, Ltd.), 10 μM) and the Smad3 inhibitor (SIS3 (Sigma-Aldrich Corp.) or SB431542 (Sigma-Aldrich Corp.); 10 μM) were added thereto. After culture for 7 days, the cells were treated with the β3 adrenaline receptor activator (norepinephrine (Wako Pure Chemical Industries, Ltd.), 1 μM) for 2 hours and then recovered.

The expression level of each gene obtained in the presence or absence of rosiglitazone is shown in FIG. 8.

As shown from FIG. 8, the expression level of UCP-1 was synergistically increased by the addition of rosiglitazone to SIS3 or SB431542 and norepinephrine.

(6) Contribution of β3 Adrenaline Receptor Activator

The preadipocytes (n=3) were inoculated to a 12-well plate coated with type I collagen. On the next day, the PPARγ activator (rosiglitazone (Rosi) (Wako Pure Chemical Industries, Ltd.), 1 μM) and the Smad3 inhibitor (SIS3 (Sigma-Aldrich Corp.), 10 μM) were added thereto. After culture for 7 days, the cells were treated with the β3 adrenaline receptor activator (norepinephrine (Wako Pure Chemical Industries, Ltd.) or mirabegron (MedChemexpress); 1 μM) for 2 hours and then recovered.

The expression level of the UCP-1 gene obtained in the presence or absence of norepinephrine or mirabegron is shown in FIG. 9.

As shown from FIG. 9, the expression level of UCP-1 was synergistically increased by the addition of norepinephrine or mirabegron to rosiglitazone and SIS3.

(7) Induction of UCP-1 by Combination of Materials

The PPARγ activator, the Smad3 inhibitor, and the β3 adrenaline receptor activator or the TGR5 activator obtained in Reference Examples described below were tested for a UCP-1 expression-inducing action using their respective materials given below.

The preadipocytes were suspended in a high glucose DMEM (Sigma-Aldrich Corp.) medium supplemented with 10% fetal bovine serum (FBS, AusGeneX PTY LTD.), 100 units/mL penicillin (Invitrogen Corp.), and 100 mg/mL streptomycin (Invitrogen Corp.), then inoculated to a 12-well plate coated with type I collagen, and cultured at 37° C. under 5% $CO_2$ conditions. On the next day, the PPARγ activator and the Smad3 inhibitor were each added thereto, followed by culture for 7 days. Then, the β3 adrenaline receptor activator or the TGR5 activator was added thereto. After 2 hours, the cells were recovered and subjected to mRNA extraction and RT-PCR to evaluate a UCP-1 mRNA expression-inducing action. The results are shown in FIG. 10. The concentrations used in the evaluation are as follows:

Rosiglitazone (Rosi): 1 μM
SIS3: 10 μM
Norepinephrine (NE): 1 μM
Plant tannin/luteolin/allspice: 0.001% (W/V)
Rosemary/clove/cinnamon/bay: 0.002% (W/V)
EPA (eicosapentaenoic acid): 100 μM
Bile acid: 10 μM
Mint/fermented guava tea/olive tea/lemon balm/hyssop/Glycyrrhiza: 0.01% (W/V)

As shown from FIG. 10, the expression level of UCP-1 was remarkably increased by the combination of these agents, i.e., the PPARγ activator, the Smad3 inhibitor, and the β3 adrenaline receptor activator or the TGR5 activator.

Example B2 UCP-1 Express Ion-Inducing Action (Mouse)

(1) Animal and Breeding Thereof

C57BL/6J mice (SLC, male, 10 weeks old) were divided into 4 groups such that the body weight was equivalent among the groups (n=10). For diet, each mouse was allowed to freely eat standard solid feed CE-2 (Oriental Yeast Co., Ltd.) and freely drink tap water. The breeding environment was set to room temperature of 23±2° C., a humidity of 55±10%, and a light period of 7 a.m. to 7 p.m.

(2) Operation to Implant Alzet Osmotic Pump

A 1/13 diluted solution of Somnopentyl was intraperitoneally administered at 10 mL/kg body weight, and then, an analgesic pentazocine was subcutaneously injected at 1 mg/kg body weight. After shaving of the back, an osmotic pump Alzet (DURECT Corp.) filled with the agents given below was implanted subcutaneously to thereby continuously administer the agents.

<Test Compound>

Group 1: control
Group 2; PPARγ activator (rosiglitazone (Rosi) (5 mg/kg body weight/day))+Smad3 inhibitor (SIS3 (5 trig/kg body weight/day))
Group 3: β3 adrenaline receptor activator (CL316,243 (0.01 mg/kg body weight/day))
Group 4: PPARγ activator (rosiglitazone (5 mg/kg body weight/day))+Smad3 inhibitor (SIS3 (5 mg/kg body weight/day))+β3 adrenaline receptor activator (CL316,243 (0.01 mg/kg body weight/day))

One week after the operation, inguinal subcutaneous fat was collected for the analysis of a UCP-1 expression level. The collected tissues were immediately frozen using liquid nitrogen and stored at −80° C. until use. The tissues were also fixed in a 10% formalin solution for staining.

(3) Quantitative PCR

Total RNA was extracted according to a standard method using RNeasy Lipid Tissue Mini Kit (Qiagen N.V.). The total RNA was reverse-transcribed according to a standard method using High Capacity RNA-to-cDNA Kit (Applied Biosystems by Life Technologies).

Quantitative PCR was performed with the cDNA (30 ng/well) obtained by reverse transcription as a template using 7500 Fast Real-Time PCR System (Applied Biosystems by Life Technologies). The expression level of the UCP-1 gene was corrected with a 36B4 gene expression level as an internal standard. The significant difference was tested using a multiple comparison test by the Tukey-Kramer method (different letters indicate significant difference with P<0.05). The measurement results are shown in FIG. 11 (left diagram).

As shown from FIG. 11 (left diagram), the expression level of UCP-1 was remarkably increased by the combination of rosiglitazone, SIS3, and CL316,243, (4) Western Blotting The inguinal subcutaneous fat was added with Lysis buffer and homogenized. After removal of solidified fat layers by centrifugation at 3,000 rpm at 4° C. for 5 minutes, a supernatant centrifuged at 12,000 rpm at 4° C. for 10 minutes was obtained as a protein solution.

A prepared sample containing 10 μg of the protein and a ¼ volume of 4×SDS Sample buffer (Novagen) per lane was thermally denatured at 95° C. for 5 minutes and then used in SDS-PAGE. The protein was transferred to Immun-Blot™ PVDF Membrane (Bio-Rad Laboratories, Inc.), subjected to blocking and antibody reaction by the procedures given below, and exposed using ECL prime western blotting detection system (Amersham plc), followed by detection of a band. The detection results are shown in FIG. 11 (right diagram).

5% skimmed milk/TBS-T, 1 hour (room temperature)
↓ Washing with TBS-T
Primary antibody/Can Get Signal™ solution 1 (Toyobo Co., Ltd.), O/N (4° C.)
↓ Washing with TBS-T
Secondary antibody/Can Get Signal™ solution 2 (Toyobo Co., Ltd.), 1 hour (room temperature)
↓ Washing with TBS-T
Detection
TBS-T: 0.1% Tween 20/tris-buffered saline (TBS)
Lysis buffer: RIPA buffer (Sigma-Aldrich Corp.), Protease inhibitor cocktail (1/1,000 amount, Sigma-Aldrich Corp.)
Primary antibody; anti-UCP-1 (Abcam #23841), diluted 1,000-fold
anti-α-tubulin (Cell signaling #2144), dilated 1,000-fold
Secondary antibody: anti-rabbit IgG, HRP linked (GE Healthcare Japan Corp.), diluted 1,000-fold As shown from FIG. 11 (right diagram), the expression level of UCP-1 was remarkably increased by the combination of rosiglitazone, SIS3, and CL316,243.

(5) Immunohistochemical Staining of UCP-1

The inguinal subcutaneous fat was subjected to the immunohistochemical staining of UCP-1 according to the protocol given below. A 10% formalin solution was used in tissue fixation. The antibody used was anti-UCP-1 (Abcam #23841). The staining results are shown in FIG. 12.
<Protocol>
1) A paraffin section is deparaffinized with xylene, washed with alcohol and water, and dipped in PBS.
2) MW treatment is performed with Dako Target Retrieval solution, pH 9 (10×) for 5 minutes.
3) After washing with PBS, treatment with 1% hydrogen peroxide in methanol is performed at room temperature for 30 minutes.
4) The resulting sample is reacted with a primary antibody diluted 300-fold at room temperature for 60 minutes.
5) After washing with PBS, the sample is reacted with Anti-Rabbit Envision at room temperature for 30 minutes.
6) After washing with PBS, color is developed with DAB, followed by nuclear staining with hematoxylin, dehydration, clearing, and embedding.
Washing with PBS: 5 minutes×3 times
<Reagent>
Primary antibody: ab23841 (Abcam plc)
Secondary antibody: Envision™ K4003 (Dako by Agilent Technologies)
DAB: K3468 (Dako by Agilent Technologies)
Dako Target Retrieval solution, pH 9: S2367 (Dako by Agilent Technologies)

As shown from FIG. 12, the cells were reduced in size and UCP-1 expression (portions stained brown) was induced by the combination of rosiglitazone, SIS3, and CL316,243.

Example B3 Energy Metabolism-Promoting Action (1) Animal and Breeding Thereof

Each C57BL/6J (SLC, male, 7 weeks old) was allowed to freely eat High-Fat Diets with 60 cal % Fat (Research Diets, Inc.) and freely drink tap water. The body weight was measured every week. After 10 weeks, the mice were divided into 4 groups such that the average body weight was equivalent among the groups (n=8). The breeding environment was set to room temperature of 23±2° C., a humidity of 55±10%, and a light period of 7 a.m. to 7 p.m.

(2) Operation to Implant Alzet Osmotic Pump

A 1/13 diluted solution of Somnopentyl was intraperitoneally administered at 10 mL/kg body weight, and then, an analgesic pentazocine was subcutaneously injected at 1 mg/kg body weight. After shaving of the back, an osmotic pump Alzet (DURECT Corp.) filled with the agents given below was implanted to thereby continuously administer the agents.
<Test Compound>
Group 1: Control
Group 2: PPARγ activator (rosiglitazone (Rosi); 5 mg/kg body weight/day)+Smad3 inhibitor (SIS3; 5 mg/kg body weight/day)
Group 3; β3 adrenaline receptor activator (CL316,243; 0.1 mg/kg body weight/day)
Group 4; PPARγ activator (rosiglitazone (Rosi); 5 mg/kg body weight/day)+Smad3 inhibitor (SIS3; 5 mg/kg body weight/day)+β3 adrenaline receptor activator (CL316,243; 0.1 mg/kg body weight/day)

(3) Breath Analysis

Each mouse was placed in a chamber for breath measurement and habituated for 3 days, followed by breath analysis using Arco-2000 system (Arco System, Inc.) for a total of 48 hours from 7 p.m. of the 10th day after the operation to 7 p.m. of the 12th day after the operation. The measurement items were set to the amount of oxygen consumed and a respiratory quotient. Also, the amount of lipid burned and the amount of carbohydrate burned were calculated according to the Peronnet's expressions given below from the amount of oxygen consumed and the respiratory quotient. The measurement was performed by switching the chamber every 15 seconds, and an average value of data was calculated every 3 minutes and used as a measurement value in the analysis. In the chamber, the mouse was raised under conditions where the mouse was allowed to freely eat High-Fat Diets with 60 cal % Fats and freely drink tap water. At the completion of the measurement, the feed intake was calculated by measuring the diet weight. The significant difference was tested using a multiple comparison test by the Tukey-Kramer method (different letters indicate significant difference with P<0.05). The average measurement value is shown in FIGS. 13 and 14.

<Peronnet's Expressions> (Peronnet F et al. (1991) Table of Nonprotein Respiratory Quotient: An Update. Can J Sport Sci 16: 23-29)

Amount of lipid burned=1.635×(1−1.701/1.695×Respiratory quotient)×Amount of oxygen consumed Amount of carbohydrate burned=(4.585×Respiratory Quotient−3.226)×Amount of oxygen consumed As shown from FIGS. 13 and 14, the amount of oxygen consumed (the amount of energy consumed) and the amount of lipid burned (the amount of lipid oxidized) were increased by the combination of rosiglitazone, SIS3, and CL316,243.

(4) Measurement of Rectal Temperature

Before and after administration of rosiglitazone, SIS3, and CL316,243 (before and after operation), the rectal temperature was measured at about 9 a.m. of the 14th day after the operation as a light period and at about 9 p.m. of the 12th day after the operation as a dark period. The measurement was performed without anesthesia and restraint using a rectal temperature measurement probe for mice. (RET-3; Physitemp Instruments, Inc.) connected to a digital thermometer. The significant difference was tested using a multiple comparison test by the Tukey-Kramer method (different letters indicate significant difference with P<0.05), The measurement results are shown in FIG. 15.

As shown from FIG. 15, the rectal temperature was significantly elevated and energy consumption (heat production) was increased by the combination of rosiglitazone, SIS3, and CL316,243.

Example B4 Carbohydrate Metabolism- and Lipid Metabolism-Improving Actions

On the 13th day after the operation to implant the Alzet osmotic pump, each animal was subjected to oral carbohydrate and lipid tolerance tests. The following solution containing 10 mass % glucose and 10 mass % corn oil was emulsified by ultrasonication and then used as a carbohydrate-lipid mixed emulsion.

<Composition of Carbohydrate-Lipid Mixed Emulsion>

| | |
|---|---|
| Glucose | 1 g |
| Corn oil | 1 g |
| Egg yolk lecithin | 0.1 g |
| Fatty acid-free BSA | 0.4 g |
| Distilled water | total 10 mL |

After fasting for 12 hours, each mouse was restrained under isoflurane anesthesia, and the carbohydrate-lipid mixed emulsion was orally administered in an amount of 10 mL/kg body weight using a probe. After 0, 15, 30, 60, and 120 minutes, blood, was collected from the orbit under isoflurane anesthesia while the blood glucose level, the serum insulin concentration, the serum triglyceride concentration (TG), and the serum free fatty acid concentration (NEFA) were measured.

The blood glucose level was measured using a simple blood glucose level meter Accu-Chek Aviva (F. Hoffmann-La Roche, Ltd.) and a measurement test paper Accu-Chek Aviva Strip II (F. Hoffmann-La Roche, Ltd.). Serum was separated from the collected blood by centrifugation at 10,000 rpm at 4° C. for 6 minutes. The serum insulin concentration was measured using an insulin measurement kit (Morinaga Institute of Biological Science, Inc.). The serum triglyceride concentration was measured using TG E-Test (Wako Pure Chemical Industries, Ltd.). The serum free fatty acid concentration was measured using NEFA C-Test (Wako Pure Chemical Industries, Ltd.). AUC was calculated from an area with the lowest measurement value as a base. The significant difference was tested using a multiple comparison test by the Tukey-Kramer method (different letters indicate significant difference with P<0.05). The measurement results are shown in FIGS. 16 and 17.

As shown from FIGS. 16 and 17, the blood glucose level, the serum insulin level, the triglyceride (TG) level, and the NEFA (fatty acid) level were remarkably decreased by the combination of rosiglitazone, SIS3, and CL316,243, demonstrating a carbohydrate metabolism-improving action and a lipid metabolism-improving action.

Example B5 Obesity-Preventing Action and Body Fat Accumulation-Inhibiting Action (1) Measurement of Body Weight Before and after the administration (before and after the operation), the body weight of each rat was measured. The measurement after the operation was performed at night of the 12th day after the operation, after the completion of the breath analysis, and before the start of fasting. The significant difference was tested using a multiple comparison test by the Tukey-Kramer method (different letters indicate significant difference with P<0.05). The difference between the value before the administration and the value after the administration is shown in FIG. 18.

As shown from FIG. 18, the body weight was reduced by the combination of rosiglitazone, SIS3, and CL316,243, demonstrating an anti-obesity action.

(2) Measurement of Adipose Tissue Weight

Anatomy was performed on the 14th day after the operation. Blood was collected from the abdominal vena cava under isoflurane anesthesia. Then, each tissue shown below was collected and the weight of the tissue was measured. The significant difference was tested using a multiple comparison test by the Turkey-Kramer method (different letters indicate significant difference with P<0.05). The measurement results are shown in FIG. 19.

As shown from FIG. 19, the white adipose weight was significantly reduced by the combination of rosiglitazone, SIS3, and CL316,243.

Example B6 Blood Analysis

Serum from the blood obtained by the anatomy described above was subjected to componential analysis using commercially available measurement kits described below. The results are shown in Table 1.

Adiponectin: adiponectin ELISA kit (Otsuka Pharmaceutical Co., Ltd.)

Insulin: insulin measurement kit (Morinaga Institute of Biological Science, Inc.)

Glucose: N-Assay Glu-UL (Nittobo Medical Co., Ltd.)

Total cholesterol: N-Assay L T-CHO-H (Nittobo Medical Co., Ltd.)

Triglyceride: N-Assay TG-H (Nittobo Medical Co., Ltd.)

NEFA: NEFA-HA Test Wako (Wako Pure Chemical Industries, Ltd.)

TABLE 1

|  | Control | Rosi + SIS3 | CL316,243 | Rosi + SIS3 + CL316,243 |
|---|---|---|---|---|
| Adiponectin [μg/ml] | 20.8 ± 0.8$^a$ | 28.7 ± 4.8$^{ab}$ | 36.9 ± 6.9$^{ab}$ | 65.6 ± 15.3$^b$ |
| Insunlin [ng/ml] | 4.81 ± 1.10$^a$ | 2.52 ± 0.58$^{ab}$ | 3.05 ± 0.30$^{ab}$ | 1.39 ± 0.15$^b$ |
| Glucose [mg/dl] | 420.1 ± 106.6$^a$ | 298.2 ± 20.7$^a$ | 274.9 ± 19.6$^a$ | 255.6 ± 27.3$^a$ |
| Total cholesterol [mg/dl] | 152.2 ± 10.6$^a$ | 119.2 ± 5.0$^b$ | 151.1 ± 4.8$^{ac}$ | 142.3 ± 5.1$^{ab}$ |
| Triglyceride [mg/dl] | 92.1 ± 12.8$^a$ | 56.2 ± 4.3$^{ab}$ | 77.2 ± 7.8$^{ab}$ | 52.0 ± 5.8$^b$ |
| NEFA [mEq/l] | 0.93 ± 0.06$^a$ | 0.75 ± 0.05$^a$ | 0.92 ± 0.09$^a$ | 0.74 ± 0.05$^a$ |

As shown from Table 1, the serum adiponectin level was increased and the insulin, glucose, triglyceride, and NEFA levels were decreased by the combination of rosiglitazone, SIS3, and CL316,243. This demonstrated that the combination of the PPARγ activator, the Smad3 inhibitor, and the β3 adrenaline receptor activator or the TGR5 activator is useful as an adiponectin production promoter, a hyperinsulinemia inhibitor, a hyperglycemia inhibitor, a hyperlipidemia inhibitor, a lipid metabolism-improving agent, a carbohydrate metabolism-improving agent, and the like.

Reference Example 1 Smad3-Inhibiting Material

HEK293 cells were inoculated at 3×10$^5$ cells/well to a 6-well dish and cultured overnight in DMEM containing 5% charcoal-treated FBS. On the next day, the medium was replaced with serum-free DMEM supplemented with each material shown in Table 2 below at a final concentration of 0.002% (luteolin: 2 μM) (low-concentration sample) or a final concentration of 0.01% (luteolin: 10 μM) (high-concentration sample). After 2 hours, 0.03 μg/mL TGF-β was added to each well, and the cells were incubated for 20 minutes. After removal of the medium, the resulting cells were washed with PBS and then recovered.

TABLE 2

| Material | Preparation method, etc. |
|---|---|
| a) Plant tannin | Obtained by extraction from the gall of *Rhus javanica* of the family Anacardiaceae with warm water. Product name "Tannic Acid AL" (Fuji Chemical Industries Co., Ltd.) was used. |
| b) Luteolin | Purchased from Kanto Chemical Co., Inc. |
| c) Rosemary extract | Obtained by extraction from the leaf or flower of *Rosmarinus officinalis* of the family Lamiaceae with carbon dioxide, warm to hot hydrous ethanol, or ethanol, or obtained by extraction therefrom with warm to hot hexane, methanol, or hydrous methanol followed by removal of the solvent. Product name "RM-21B Base" (Mitsubishi-Kagaku Foods Corp.) was used. |
| d) White tea extract | Extract of white tea prepared from the leaf of *Camellia sinensis* L. Purchased from Organic Herb Inc. |
| e) Milk thistle extract | Extract from the seed of *Silybum marianum* of the family Asteraceae. Purchased from Kenko Corp. |
| f) Logwood extract | Obtained by extraction from the core of *Haematoxylon campechianum* of the family Febaceae with hot water. Product name "Hematein" (ICHIMARU PHARCOS Co., Ltd.) was used. |
| g) Peanut testa extract | Extract from the testa of *Arachis hypogaea* L. of the family Febaceae. Purchased from Tokiwa Phytochemical Co., Ltd. |
| h) *Litchi* polyphenol | Produced and obtained by extraction from the fruit of *Litchi chinensis* of the family Sapindaceae followed by mixing with a green tea extract and depolymerizing with heat. Product name "Oligonol" (AMINO UP CHEMICAL Co., Ltd.) was used. |
| i) Apple polyphenol | Produced and obtained by squeezing extraction from the immature fruit of *Malus pumila* of the family Rosaceae followed by resin purification. Product name "Applephenon C-100" (Asahi Group Foods, Ltd.) was used. |
| j) Oolong tea extract | Obtained by extraction, with hot water, from semifermented tea (oolong tea) produced from the leaf of *Camellia sinensis* of the family Theaceae. Product name "Oolong Tea Extract" (San-Ei Gen F.F.I., Inc.) was used. |
| k) Allspice | Obtained by extraction from the fruit of *Pimenta dioica* of the family Myrtaceae with a 50% aqueous ethanol solution. |

(Western Blotting)

The recovered cells were added with Lysis buffer and well homogenized. The cells were left to stand for 15 minutes on ice and then ultrasonically disrupted, and a supernatant centrifuged at 12,000 rpm at 4° C. for 10 minutes was obtained as a protein solution.

A prepared sample containing 25 mg of the protein and a ¼ volume of 4×SDS Sample buffer (Novagen) per lane was thermally denatured at 95° C. for 5 minutes and then used in SDS-PAGE. The protein was transferred to Immun-Blot™ PVDF Membrane (Bio-Red Laboratories, Inc.) and subjected to blocking and antibody reaction by the procedures given below, and α-Tubulin and Smad3 were detected together using ECL prime western blotting detection system (Amersham plc). In FIG. 20, (−) depicts that TGF-β was not added, and (+) depicts that TGF-β was added.
5% skimmed milk/TBS-T, 1 hour (room temperature)
↓ Washing: with TBS-T
Primary antibody/Can Get Signal™ solution 1 (Toyobo Co., Ltd.), O/N (4° C.)
↓ Washing with TBS-T
Secondary antibody/Can Get Signal™ solution 2 (Toyobo Co., Ltd.), 1 hour (room temperature)
↓ Washing with TBS-T
Detection
TBS-T; 0.1% Tween 20/tris-buffered saline (TBS)
Lysis buffer: RIPA buffer (Sigma-Aldrich Corp.)
Protease inhibitor cocktail (1/1,000 amount, Sigma-Aldrich Corp.)
Phosphatase Inhibitor Cocktail 1 (1/100 amount, Sigma Aldrich Corp.)
Phosphatase Inhibitor Cocktail 2 (1/100 amount, Sigma-Aldrich Corp.)
Primary antibody: anti-Smad3 (Cell signaling #9513), diluted 1,000-fold
anti-phospho Smad3 (Cell signaling #9520), diluted 1,000-fold
anti-α-tubulin (Cell signaling #2144), diluted 1,000-fold
Secondary antibody: anti-rabbit IgG, HRP linked (GE Healthcare Japan Corp.), diluted 1,000-fold
As for the materials a) to k), TGF-β stimulation-responsive Smad3 hyperphosphorylation was inhibited, and a more remarkable inhibiting effect was observed in the high-concentration treatment group (right lanes) (FIG. 20).

Reference Example 2 PPARγ-Activating Material

An African green monkey kidney cell line CV-1 was seeded over a plate and cultured in DMEM (5% charcoal-treated fetal bovine serum) for 1 day. The cells were cotransfected with a reporter plasmid (pG5-Luc; Invitrogen Corp.) containing a GAL4-binding sequence upstream of firefly luciferase gene, and pBIND-PPARγ-LBD which was a pBIND vector (Promega Corp) having an insert of a human PPARγ2 ligand-binding site (NCBI Ref Seq NM_015869, nt703-1606) using a transfection reagent (Superfect Transfection Reagent; Qiagen N.V.). The pBIND-PPARγ-LBD vector causes expression of a fusion protein of the PPARγ2 ligand-binding site and a site binding to the GAL4-binding sequence in the transfected cells. This fusion protein binds to the PPARγ2 ligand and thereby activates transcription of the firefly luciferase gene located downstream thereof. Accordingly, the amount of the PPARγ2 ligand bound can be determined by measuring the firefly luciferase activity. In addition, the vector also harbors *Renilla* luciferase gene. Therefore, the transfection efficiency of the vector can be determined by measuring the *Renilla* luciferase activity. 3 hours after the transfection with the vector the culture solution was replaced with DMEM (5% charcoal-treated fetal bovine serum). After another 2 hours, the culture solution was replaced with a serum-free DMEM medium supplemented with each material at the described final concentration shown in Table 3 below. After culture for approximately 16 hours, the cells were washed with PBS and evaluated for a PPARγ-activating action by measurement of firefly and *Renilla* luciferase activities using Dual Luciferase Reporter Assay System (Promega Corp.). The PPARγ-activating action was defined as follows: PPARγ-activating action=(Firefly luciferase activity from pG5-Luc)/(*Renilla* luciferase activity from GAL4-PPARγ-LBD).

The results were indicated by relative values to the luciferase activity in a control defined as 1.

TABLE 3

| Material | Preparation method, etc. |
|---|---|
| a) *Davana* extract (0.005%) | Obtained by steam distillation from the above-ground part of *Artemisia pallens* of the family Asteraceae. Product name "OIL DAVANA (*ARTEMISIA PALLENS*)" (*CITRUS* AND ALLIED ESSENCES Ltd.) was used. |
| b) Elemi extract (0.005%) | Oleoresin of the secretion of *Canarium luzonicum* of the family Burseraceae. Product name "ELEMI OIL EXTRA" (PAYAN BERTRAND S.A.) was used. |
| c) Clove extract (0.005%) | Obtained by steam distillation from the bud of *Syzygium aromaticum* of the family Myrtaceae. |
| d) *Citronella* extract (0.005%) | Obtained by steam distillation from the entire plant of *Cymbopogon nardus* or *Cymbopogon winterianus* of the family Poaceae. Product name "*CITRONELLA* OIL" (Ogawa & Co., Ltd.) was used. |
| e) Bay extract (0.005%) | Obtained by steam distillation from the leaf of *Pimenta racemosa* of the family Myrtaceae. Product name "OIL BAY" (CHARABOT, Japan) was used. |
| f) Hemp seed extract (0.005%) | Obtained by extraction from the fruit of *Cannabis sativa* of the family Cannabaceae with 50% ethanol. |
| g) Ashitaba chalcone (0.005%) | Obtained by juice squeezing from the stem of *Angelica keiskei* of the family Apiaceae. Product name "Ashitaba Chalcone Powder) (Japan Bio Science Laboratory Co., Ltd.) was used. |
| h) Poppy seed extract (0.005%) | Obtained by extraction from the fruit of *Papavar somniferum* of the family Papaveraceae with 50% ethanol. |
| i) Lovage extract (0.005%) | Obtained by steam distillation from the root of *Levisticum officinale* of the family Apiaceae. Product name "LOVAGE ROOT AT 100" (H. REYNAUD & FILS) was used. |

TABLE 3-continued

| Material | Preparation method, etc. |
|---|---|
| j) Ginger extract (0.005%) | Obtained by steam distillation from the rhizome of *Zingiber officinale* of the family Zingiberaceae.<br>Product name "Spice Extract Preparation Ginger SP-23977" (San-Ei Gen F.F.I., Inc.) was used. |
| k) Cinnamon extract (0.005%) | Obtained by steam distillation from the bark of *Cinnamomum zeylanicum* of the family Lauraceae.<br>Product name "CINNAMON CEYLON OIL EXTRA" (PAYAN BERTRAND S.A.) was used. |
| l) DHA (500 μM) | Purchased from Sigma-Aldrich Corp. |
| m) EPA (500 μM) | Purchased from Sigma-Aldrich Corp. |
| n) Nutmeg extract (0.005%) | Obtained by steam distillation from the seed or aril of *Myristica fragrans* of the family Myristicaceae.<br>Product name "NUTMEG OIL" (AROMA & CO. CV) was used. |

As shown from FIG. 21, the materials a) to n) were found to activate PPARγ.

Reference Example 3 TGR5-Activating Material

HEK293 cells were inoculated at $1.0 \times 10^5$ cells/well to a 24-well plate and cultured in a DMEM medium containing 5% charcoal-treated FBS for 1 day. Then, the cells were transfected with 200 ng/well of a firefly luciferase reporter vector pGL4.29[luc2P/CRE/Hygro](Promega Corp.) containing a cAMP-responsive element (CRE), 40 ng/well of a human TGR5 expression vector hTGR5 (pcDNA3.1+), and 80 ng/well of phRL-TK (*Renilla* luciferase vector for gene, transfection efficiency correction) using Superfect transfection reagent (Qiagen N.V.). After 3 hours, the medium was replaced with a DMEM medium containing 5% charcoal-treated PBS. After another 4 hours, each material shown in Table 4 below was added thereto at a final concentration of 0.001%. 12 to 18 hours thereafter, the luciferase activities were measured using DualGlo luciferase assay system (Promega Corp.). The TGR5-activating action was evaluated by correcting the firefly luciferase activity with the *Renilla* luciferase activity. The TGR5-activating action was indicated by relative values to the TGR5 activity in a control defined as 1.

TABLE 4

| Material | Preparation method, etc. |
|---|---|
| a) Cholic acid | Purchased from Wako Pure Chemical Industries, Ltd. |
| b) Mint extract | 50% EtOH extract from the leaf of *Mentha arvensis* L. var. *piperascens* Malinv of the family Lamiaceae.<br>1000 ml of a 50% aqueous ethanol solution was added to 100 g of Mint (obtained from Shinwa Bussan Co., Ltd.), followed by extraction at room temperature for 7 days under stand still conditions. Then, an extract was obtained by filtration. The solid concentration of the extract was 1.65% (w/v). |
| c) Fermented guava tea extract | 70% ethanol extract from fermented guava tea leaf. Purchased from Ryukyu Bio-Resource Marketing Co., Ltd. |
| d) Olive tea extract | Produced in the same way as in tea from the leaf of *Olea europaea* of the family Oleaceae.<br>Olive Extract Powder (obtained from Nippon Funmatsu Yakuhin Co., Ltd.) was dissolved at a concentration of 1% (w/v) in 40% ethanol to prepare a test sample. |
| e) Olive leaf extract | Hydrous ethanol extract from the leaf of *Olea europaea*. Purchased from Kenko Corp. |
| f) Lemon balm extract | Hydrous ethanol extract from the leaf of *Melissa officinalis* L. of the family Lamiaceae.<br>Lemon Balm Extract (obtained from Kenko Corp.) was dissolved (1% w/v) in 20% ethanol and used. |
| g) Hyssop extract | 50% aqueous ethanol extract from the entire plant of *Hyssopus officinalis* L. of the family Lamiaceae.<br>Hyssop (purchased from Tochimoto Tenkaido Co., Ltd.) was supplemented with a 10-fold amount of 50% aqueous ethanol and immersed therein at room temperature for 7 days, followed by filtration to obtain an extract. The solid concentration of the extract was 1.76%. |
| h) *Glycyrrhiza* extract | Obtained by extraction with hot water from residues from the washing of the root or rhizome of *Glycyrrhiza uralensis* FISCHER, *Glycyrrhiza inflata* BATALIN, or *Glycyrrhiza glabra* LINNE of the family Fabaceae with water, or obtained by extraction therefrom with an alkaline aqueous solution at room temperature or under slight warming followed by purification.<br>Glycymin M (trade name; purchased from Maruzen Pharmaceuticals Co., Ltd.) was dissolved (1% w/v) in 50% ethanol and used. |
| i) Hawthorn berry extract | 45% ethanol extract from the leaf or flower of *Crataegus oxyacantha* L. Purchased from Ask Intercity Co., Ltd. |

TABLE 4-continued

| Material | Preparation method, etc. |
| --- | --- |
| j) Marjoram extract | 50% ethanol extract from the entire plant of *Origanum majorana* of the family Lamiaceae.<br>100 ml of a 50% aqueous ethanol solution was added to 10 g of Marjoram (obtained from Tochimoto Tenkaido Co., Ltd.), followed by extraction at room temperature for 7 days under stand still conditions. Then, an extract was obtained by filtration. The solid concentration of the extract was 2.22% (w/v). |
| k) Mate tea extract | Hydrous ethanol extract from the leaf of *Ilex paraguariensis* of the family Aquifoliaceae.<br>Mate Extract (obtained from Kenko Corp.) was dissolved at a concentration of 1% (w/v) in 20% ethanol to prepare a test sample. |
| l) Banaba leaf extract | Ethanol extract from the leaf of *Lagerstroemia speciose*. Purchased from Kenko Corp. |
| m) *Perilla* extract | Red Shiso Powder (Kodama Foods Co., Ltd.) dissolved in DMSO. |
| n) Soybean saponin | Purchased from Tokiwa Phytochemical Co., Ltd. |
| o) *Jujube* seed extract | Obtained by extraction from the seed of *Ziziphus jujuba* of the family Rhamnaceae with 50% ethanol.<br>1000 ml of a 50% aqueous ethanol solution was added to 100 g of *Jujube* seeds (obtained from Shinwa Bussan Co., Ltd.), followed by extraction at room temperature for 7 days under stand still conditions. Then, an extract was obtained by filtration. The solid concentration of the extract was 0.95% (w/v). |
| p) Basil extract | Obtained by steam distillation from the entire plant of *Ocimum basilicum* of the family Lamiaceae.<br>Basil SP-71887 (obtained from San-Ei Gen F.F.I., Inc.) was used. |
| q) *Lotus* root extract | Obtained by extraction from the rhizome of *Nelumbo nucifera* of the family Nymphaeaceae with 50% ethanol.<br>1000 ml of a 50% aqueous ethanol solution was added to 100 g of *Lotus*<br>Root Powder (obtained from Kodama Foods Co., Ltd.), followed by extraction at room temperature for 7 days under stand still conditions. Then, an extract was obtained by filtration. The solid concentration of the extract was 1.98% (w/v). |
| r) Persimmon leaf tea extract | Obtained by extraction from the leaf of *Diospyros kaki* of the family Ebenaceae with 50% ethanol.<br>1000 ml of a 50% aqueous ethanol solution was added to 100 g of Persimmon Leaf (obtained from Tochimoto Tenkaido Co., Ltd.,), followed by extraction at room temperature for 7 days under stand still conditions. Then, an extract was obtained by filtration. The solid concentration of the extract was 1.0% (w/v). |
| s) Dill extract | Obtained by steam distillation from the entire plant of *Ocimum basilicum* of the family Lamiaceae.<br>Dill Liquid SP-77544 (obtained from San-Ei Gen F.F.I., Inc.) was used. |
| t) Spearmint extraxt | 50% ethanol extract from the entire plant of *Mentha spicata* of the family Lamiaceae.<br>1000 ml of a 50% aqueous ethanol solution was added to 100 g of Spearmint (obtained from Tochimoto Tenkaido Co., Ltd.,), followed by extraction at room temperature for 7 days under stand still conditions. Then, an extract was obtained by filtration. The solid concentration of the extract was 2.10% (w/v). |
| u) Blackcurrant dye | Obtained by extraction from the fruit *Ribes nigrum* of the family Saxifragaceae with hydrous ethanol.<br>Blackcurrant Extract (obtained by Kenko Corp.) was dissolved at an extract concentration of 1% (v/v) in 50% (v/v) aqueous ethanol and used. |
| v) *Bacopa monniera* extract | Obtained by extraction from the leaf and stem of *Bacopa monniera* of the family Fabaceae with hydrous ethanol.<br>*Bacopa Monniera* Extract (obtained from Organo Foodtech Corp.) was dissolved at a concentration of 1% (w/v) in 50% EtOH and used. |
| w) Saponin | Obtained by pulverization of the seed of *Glycine max* of the family Leguminosae, extraction with water or ethanol, and purification.<br>Soy Health SA (obtained by Fuji Oil Co., Ltd.) was dissolved at a concentration of 1% (w/v) in 50% EtOH to prepare a test sample. |
| x) Nutmeg extract | Obtained by steam distillation from the seed or aril *Myristica fragrans* of the family Myristicaceae.<br>Nutmeg Liquid SP-77543 (obtained from San-Ei Gen F.F.I., Inc.) was used. |
| y) Gingerol | Purchased from Sigma-Aldrich Corp. |
| z) Loquat tea extract | Extract from the leaf of *Eriobotrya japonica* of the family Rosaceae.<br>Loquat Leaf Extract Powder (manufactured by Matsuura Yakugyo Co., Ltd.) was dissolved at a concentration of 1% (w/v) in 50% ethanol to prepare a test sample. |
| aa) Red ginger extract-P | Hydrous ethanol extract from the rhizome of *Zingiber officinale* var. *rubrum*. Purchased from Oryza Oil & Fat Chemical Co., Ltd. |
| ab) Chaste tree extract | Aqueous ethanol extract from the seed of *Vitex agnus-castus*. Purchased from Kenko Corp. |

As shown from FIG. 22, the materials a) to ab) were found to activate the TGR5 activity.

What is claimed is:

1. A composition that is a UCP-1 (uncoupling protein-1) expression promoter in a subject comprising 1-10 µM rosiglitazone or pioglitazone as a PPARy (peroxisome proliferator-activated receptor y) activator, and 10 µM SIS3 (specific inhibitor of Smad3) as a Smad3 inhibitor wherein ingestion or administration of the composition results in a synergistic increase in expression of the UCP-1 gene in adipose tissue, as compared to UCP-1 gene expression under the same conditions except that the PPARy activator is not ingested or administered.

2. A method for promoting UCP-1 (uncoupling protein-1) expression in a subject in need thereof comprising ingesting or administering 5 mg/kg/day rosiglitazone or pioglitazone as a PPARy (peroxisome proliferator-activated receptor y) activator and 5 mg/kg/day SIS3 (specific inhibitor of Smad3) as a Smad3 inhibitor in combination in the subject wherein the ingesting or administering results in a synergistic increase in expression of the UCP-1 gene in adipose tissue, as compared to UCP-1 gene expression under the same conditions except that the PPARy activator is not ingested or administered.

3. A composition that is a UCP-1 (uncoupling protein-1) expression promoter in a subject comprising 1-10 µM rosiglitazone or pioglitazone as a PPARy (peroxisome proliferator-activated receptor y) activator, and 10 µM SIS3 (specific inhibitor of Smad3) as a Smad3 inhibitor and 1 µm CL316,243 as a β3 adrenaline receptor activator wherein ingestion or administration of the composition results in a synergistic increase in expression of the UCP-1 gene in adipose tissue, as compared to UCP-1 gene expression under the same conditions except that the PPARy activator is not ingested or administered.

4. A method for promoting UCP-1 (uncoupling protein-1) expression in a subject in need thereof comprising combining ingestion or administration of 5 mg/kg/day rosiglitazone or pioglitazone as a PPARy (peroxisome proliferator-activated receptor y) activator and ingestion or administration of 5 mg/kg/day SIS3 (specific inhibitor of Smad3) as a Smad3 inhibitor and ingestion and administration of 0.01-0.1 mg/kg/day CL316,243 as a β3 adrenaline receptor activator in the subject wherein the ingestion or administration results in a synergistic increase in expression of the UCP-1 gene in adipose tissue, as compared to UCP-1 gene expression under the same conditions except that the PPARy activator is not ingested or administered.

5. The method according to claim 2 wherein the PPARy activator is pioglitazone.

6. The method according to claim 2 wherein the PPARy activator is rosiglitazone.

7. The method according to claim 4 wherein the PPARy activator is rosiglitazone.

* * * * *